United States Patent
Murtagh et al.

(10) Patent No.: US 7,616,307 B2
(45) Date of Patent: Nov. 10, 2009

(54) OPTICAL MEASUREMENT APPARATUS AND METHOD

(75) Inventors: Martin Edward Murtagh, Carrigaline (IE); Patrick Vincent Kelly, Galway (IE); Michael Geoffrey Somekh, Wollaton Nottingham (GB); Mark Charles Pitter, Nottingham (GB); Stephen David Sharples, Nottingham (GB)

(73) Assignee: KLA-Tencor Corporation, Milpitas, CA (US)

( * ) Notice: Subject to any disclaimer, the term of this patent is extended or adjusted under 35 U.S.C. 154(b) by 118 days.

(21) Appl. No.: 12/061,542

(22) Filed: Apr. 2, 2008

(65) Prior Publication Data

US 2009/0033931 A1    Feb. 5, 2009

Related U.S. Application Data

(63) Continuation of application No. PCT/IE2006/000118, filed on Oct. 24, 2006.

(60) Provisional application No. 60/729,233, filed on Oct. 24, 2005, provisional application No. 60/749,597, filed on Dec. 13, 2005.

(51) Int. Cl.
*G01J 3/26* (2006.01)

(52) U.S. Cl. .................................................. 356/326
(58) Field of Classification Search ................. 356/326, 356/445
See application file for complete search history.

(56) References Cited

U.S. PATENT DOCUMENTS

| | | | |
|---|---|---|---|
| 7,280,215 B2 * | 10/2007 | Salnik et al. | 356/445 |
| 7,362,441 B2 * | 4/2008 | Opsal et al. | 356/445 |
| 2005/0099623 A1 * | 5/2005 | Takeuchi et al. | 356/317 |
| 2005/0213100 A1 * | 9/2005 | Murtagh et al. | 356/432 |

* cited by examiner

*Primary Examiner*—Kara E Geisel
(74) *Attorney, Agent, or Firm*—Luedeka, Neely & Graham, P.C.

(57) ABSTRACT

An optical modulation spectroscopy system comprises a probe beam source and components for directing the probe beam at a sample. It also may comprise a modulated pump beam source and components for directing a modulated pump beam at the sample. A dispersive system may disperse the reflected probe beam into constituent wavelengths to provide dispersed beams. A detector array may detect multiple dispersed reflected probe beams and processes a signal corresponding to each. Thus, measurement may be multiplexed for very fast performance.

28 Claims, 8 Drawing Sheets

OPTICAL MEASUREMENT APPARATUS AND METHOD

RELATED APPLICATIONS

This application is a continuation of International Application No. PCT/IE2006/000118, filed Oct. 24, 2006, which claims the benefit of Provisional Applications Nos. 60/729,233, filed Oct. 24, 2005, and 60/749,597, filed Dec. 13, 2005, the disclosures of which are incorporated herein in their entirety.

INTRODUCTION

1. Field of the Invention

The invention relates to an optical measurement apparatus and method, particularly using modulation spectroscopy.

2. Prior Art Discussion

Modulation spectroscopy is a class of spectroscopy in which the reflectance or transmission of a sample is altered at some parts of the electromagnetic spectrum by means of an external perturbation. Generally, this perturbation is applied in a periodic manner, such that the reflectance or transmission of the semiconductor at the wavelengths where it changes in response to the external perturbation, periodically alternates between the value in the absence of external perturbation, and that which it has in the presence of the external perturbation.

In some methods of modulation spectroscopy, the perturbation is optically applied by means of a light beam. In such methods, the light beam used to perform the spectroscopy measurement is often referred to as the "probe" beam and the light beam which perturbs the reflectance or transmission of the material is generally referred to as the "pump" beam. The pump beam is generally coincident with the probe beam on the sample and is modulated between being present and absent at the area of coincidence with the probe beam. The probe beam reflectance from the sample is modulated by the periodic incidence of the pump beam overlapping the same area of incidence as the probe beam. The amount of the modulation of the probe beam reflectance is generally different at different wavelengths of the probe beam.

Modulation spectroscopy requires the simultaneous detection and measurement of a small periodically modulated signal and a large time-invariant signal. Both signals are generated by a detector, which receives the reflected probe beam and generates the said signals as electrical signals. The reflected probe beam varies periodically in its intensity, generally by different amounts at different wavelengths. The modulation spectroscopy method consists of the measurement of the modulated reflectance ($\Delta R$) as a ratio to the unmodulated reflectance (R) as a function of the wavelength of the probe beam over some range of wavelengths.

The measurement of the modulated reflectance ($\Delta R$) signal has some difficulties. The modulated reflectance ($\Delta R$) signal is relatively small, even at wavelengths at which it is maximum, compared to the unmodulated reflectance (R). In any apparatus, various sources of optical and electrical noise will be present, and these can dominate the modulated reflectance ($\Delta R$) signal. However, the modulated reflectance ($\Delta R$) signal is always present at a known frequency (or in some cases where a heterodyne modulation apparatus is used, more than one known frequency), and as a result, methods of signal recovery can be employed to lock in to detect a signal at this or these known frequencies and to discriminate against other frequencies of alternating or periodic signal. The method known as phase-sensitive detection or lock-in amplification is the most common of these methods.

The requirement to use a method such as phase-sensitive lock-in amplification for the measurement of modulated reflectance ($\Delta R$) signal, requires at least a measurement at each wavelength with the pump laser beam present and absent, in order to establish the modulation ($\Delta R$). This has heretofore required that the measurement be made at different times for each wavelength at which it is desired to make a measurement, because of the requirement for an apparatus for lock-in amplification capable of measuring both the in-phase and quadrature components of the modulated reflectance ($\Delta R$) signal, as well as the phase angle of the modulated reflectance ($\Delta R$) signal, at each wavelength in the spectral range of interest. Speed of the measurement is a problem, and has precluded its widespread industrial application in high-speed production line inspection of semiconductor wafers.

A known method of high throughput photoreflectance, is due to Chichester et al, in U.S. Pat. No. 5,982,499, which teaches a method of replicating the serial (single wavelength at a time) method of acquiring the photoreflectance spectrum, at multiple points over a semiconductor wafer, using multiple probe beams and multiple detectors. This method suffers from a number of difficulties and impracticalities, chief of which is the engineering difficulty and cost of producing a large number of optical pump and probe beams, with sufficient uniformity of illumination, at multiple sites on a sample wafer. The use of multiple detectors in conjunction with a dispersing means is described in U.S. Pat. No. 5,365,334, but this relies on a phase filter which only selects the component of the photoreflectance signal which is in-phase with the reference signal from the modulator.

SUMMARY OF THE INVENTION

According to the invention, there is provided an optical modulation spectroscopy system comprising:
  a probe beam source;
  a probe beam directed at a sample to give rise to a reflected probe beam,
  a pump beam source,
  a modulator for modulating a pump beam,
  a modulated pump beam directed at a sample,
  a dispersive system for dispersing the reflected probe beam into constituent wavelengths to provide dispersed beams, and
  a detection system for detecting a plurality of the dispersed reflected probe beams, and for processing a signal corresponding to each, the detection system comprising: an array of detectors and a circuit, with a detector for detecting each of at least some of said dispersed beams; and each detector produces as output an electrical signal which comprises both a DC signal, proportional to the reflectance of a dispersed beam and an AC modulated signal at the modulation frequency proportional to the modulation of the reflectance of a dispersed beam.

In one embodiment, each detector is a photodetector pixel.

In one embodiment, the DC signal is larger relative to the AC signal and the dynamic range of the detector is sufficient to detect both the DC signal and the AC signal.

In one embodiment, the circuit provides clock and control pulses to the detectors and a synchronised reference waveform signal to the modulator.

In another embodiment, the detection system comprises means for measuring simultaneously each dispersed beam by multiplexed readout of signals from the detectors at a plurality of times at known phase steps during each period of the modulation, and the detection system calculates the photoreflectance signal (ratio $\Delta R/R$) using a phase stepping demodulation algorithm applied to the multiple measurements at the known phase steps during each period of the modulation, to give a photoreflectance spectrum.

In one embodiment, the detection system determines components of ΔR which are in-phase and quadrature relative to the phase of the reference signal, and determines the in-phase and quadrature photoreflectance signals ratio ΔR/R at a plurality of beam photon energies to give the photoreflectance spectrum.

In one embodiment, the detection system adds an arbitrary phase angle to the phase step angle used in the phase stepping demodulation algorithm such that the entire modulated reflectance signal ΔR and the photoreflectance signal (ratio ΔR/R) are adjusted such that they are in-phase with the reference signal.

In one embodiment, the detection system performs a readout a plurality of times, each corresponding to a period of the modulation.

In another aspect, the invention provides a modulation spectroscopy method carried out by a modulation spectroscopy system, the method comprising:

directing a probe beam at a sample to give rise to a reflected probe beam;

modulating a pump beam, and directing the modulated pump beam at the sample;

dispersing the reflected probe beam with a dispersive system into constituent wavelengths to provide dispersed beams;

detecting a plurality of the dispersed reflected probe beams with a detection system and processing a signal corresponding to each, with the detection system comprising:

an array of detectors and a circuit, with a detector detecting each of at least one of said dispersed beams; and each detector produces as output an electrical signal which comprises both a DC signal, proportional to the reflectance of a dispersed beam and an AC modulated signal at the modulation frequency proportional to the modulation of the reflectance of a dispersed beam.

In one embodiment, the DC signal is larger relative to the AC signal and the dynamic range of the detector is sufficient to detect both the DC signal and the AC signal.

In one embodiment, the circuit provides clock and control pulses to the detectors and a synchronised reference waveform signal to the modulator.

In one embodiment, the detection system measures simultaneously each dispersed beam by multiplexed readout of signals from the detectors at a plurality of times at known phase steps during each period of the modulation, and the detection system calculates the photoreflectance signal (ratio ΔR/R) using a phase stepping demodulation algorithm applied to the multiple measurements at the known phase steps during each period of the modulation, to give a photoreflectance spectrum.

In one embodiment, the detection system determines components of ΔR which are in-phase and quadrature relative to the phase of the reference signal, and determines the in-phase and quadrature photoreflectance signals ratio ΔR/R at a plurality of beam photon energies to give the photoreflectance spectrum.

In one embodiment, the detection system adds an arbitrary phase angle to the phase step angle used in the phase stepping demodulation algorithm such that the entire modulated reflectance signal ΔR and the photoreflectance signal (ratio ΔR/R) are adjusted such that they are in-phase with the reference signal.

In one embodiment, the detection system performs a readout a plurality of times, each corresponding to a period of the modulation.

In one embodiment, a part of the photoreflectance spectrum varies in magnitude at different probe beam photon energies and comprises one or more photoreflectance lineshapes.

In one embodiment, the sample is a semiconductor, semiconductor crystal structure, or a semiconductor wafer comprising one or more semiconductor devices and structures, and the pump beam is provided by a light source whose photon energy is at least greater than the fundamental bandgap energy of one of the semiconductors, and at least one photoreflectance lineshape is measured which corresponds to a direct interband electronic transition in the semiconductor layer.

In one embodiment, the photoreflectance lineshape is analyzed to yield the energy of the direct interband electronic transition.

In one embodiment, the photoreflectance lineshape is analyzed to yield one or more of the energy, the broadening parameter, the amplitude and the phase of the direct interband electronic transition.

In one embodiment, the photoreflectance lineshape is analyzed to yield a quantum well or quantum dot transition energy in part of all of the sample.

In one embodiment, the photoreflectance lineshape is analyzed to yield an intersubband transition energy in part or all of the sample.

In one embodiment, the photoreflectance lineshape is analyzed to yield an electric field strength in part or all of the sample.

In one embodiment, at least two photoreflectance lineshapes are measured which correspond to at least two direct interband electronic transitions in either the same or different semiconductor layers which have generated them, and the photoreflectance lineshapes are analyzed to yield the energy of these direct interband electronic transitions, or an intersubband transition energy, or a quantum well or quantum dot transition energy or the broadening parameter, the amplitude and the phase of these transitions, or to yield an electric field strength in part of all of the sample.

In one embodiment, the method comprises the further steps of analyzing the energy of one or more of the direct interband electronic transitions, measured by photoreflectance spectroscopy, to measure the strain in the semiconductor layer to which it is associated.

In one embodiment, the method comprises the further steps of analyzing one or more of the energy, the broadening parameter, the amplitude and the phase, of one or more of the direct interband electronic transitions, measured by photoreflectance spectroscopy, to measure parameters relating to crystallinity (damage/disorder) to the semiconductor or its surface.

In one embodiment, the method comprises the further steps of analyzing the energy of one or more of the direct interband electronic transitions, measured by photoreflectance spectroscopy, to measure the alloy mole fraction in the semiconductor layer to which it is associated.

In one embodiment, the method comprises the further steps of analyzing the energy of one or more of the direct interband or intersubband electronic transitions, measured by photoreflectance spectroscopy, to measure the sheet carrier concentration in the semiconductor layer to which it is associated.

In one embodiment, the method comprises the further steps of performing the measurement at a multiplicity of angles of incidence, and of performing an analyzis of the photoreflectance spectra to determine the quantum well transition energy in a semiconductor structure which is constructed to have an optical cavity, such as a semiconductor structure used for making a laser diode, a light emitting diode, a vertical cavity surface emitting laser or a resonant cavity light emitting diode.

DETAILED DESCRIPTION OF THE INVENTION

The invention will be more clearly understood from the following description of some embodiments of the apparatus thereof, given by way of example only with reference to the accompanying drawings in which.

DESCRIPTION OF THE EMBODIMENTS

Figure 1:
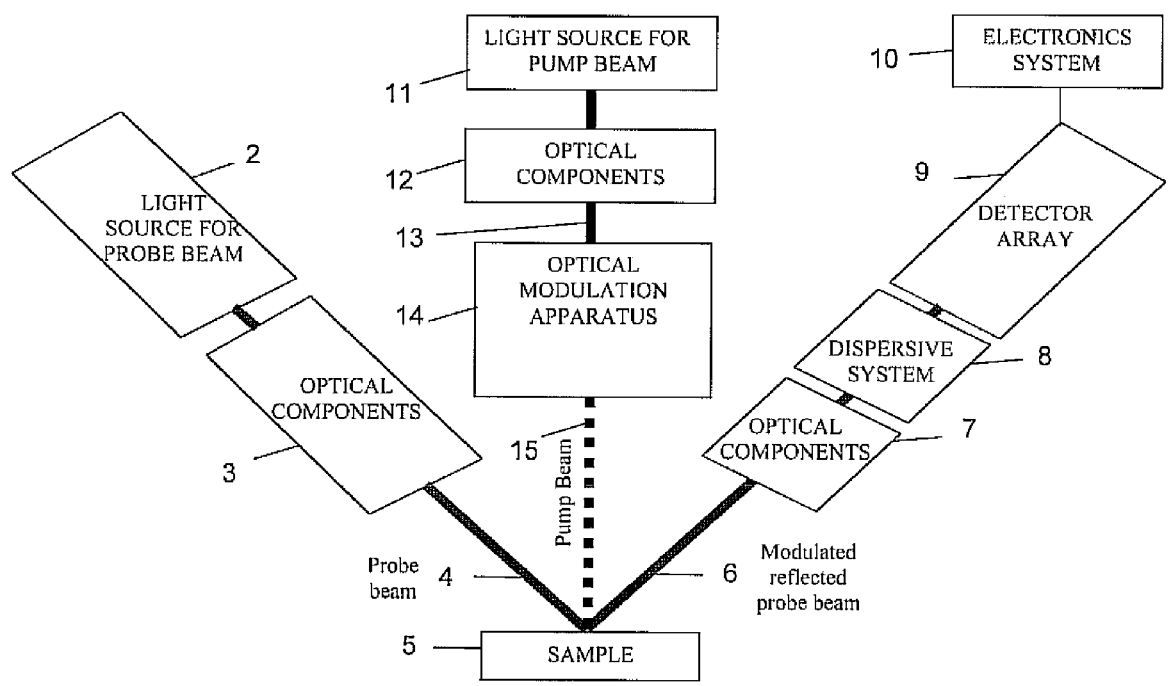
FIG. 1 is a diagrammatic overview of a measurement system of the invention according to embodiments.
Figure 2:
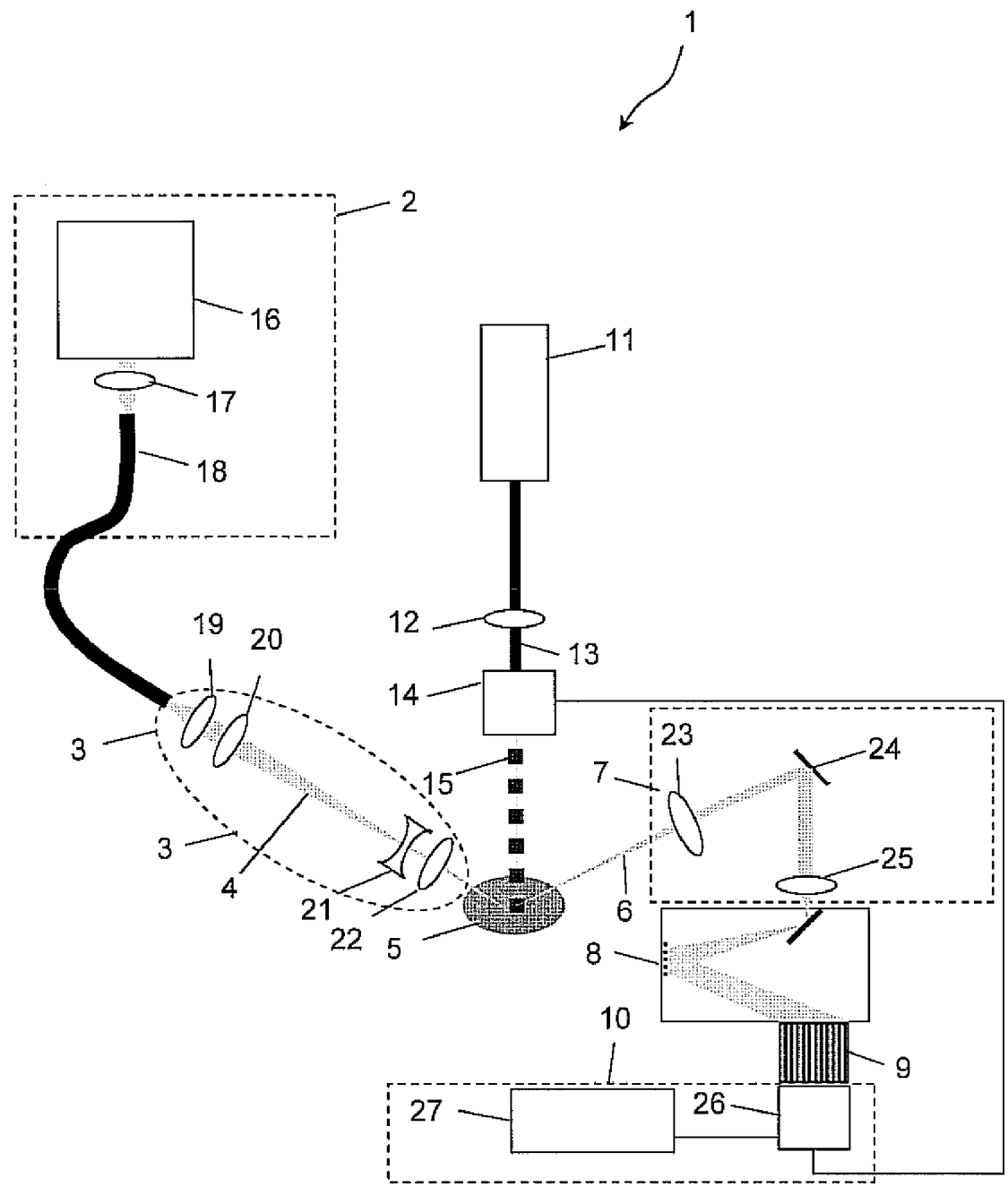
FIG. 2 is a more detailed diagrammatic view of the system according to embodiments.

Referring to FIGS. 1 and 2 a probe beam light source 2 generates an incident probe beam 4 and directs it through optical components 3 onto a sample 5. A modulated reflected probe beam 6 is routed through optical components 7 and is dispersed into its constituent wavelengths by a dispersive system 8. The dispersed wavelengths are detected by an array of probe beam detector pixels 9, each detector pixel of which detects light from a narrow range of the constituent wavelengths of the probe beam such that the entire array of detector pixels 9 detects light over a broader wavelength range of the probe beam. Also, the pump beam 13 is modulated by a modulator 14 and the modulated pump beam is indicated by 15.

The dispersive system, which in some embodiments is a spectrograph, spatially disperses the light into its constituent wavelengths such that the photoreflectance signal can be measured at a multiplicity of wavelengths. Light from each narrow band of wavelengths is incident on a different pixel of the array 9, so that the light signal can be measured simultaneously by multiplexed readout using a sufficiently fast electronics system 10 to read the signal from each detector.

The electronics system is capable of reading the modulated reflectance signal as well as the reflectance signal from each pixel of the detector array 9 in sufficiently rapid succession, such that multiple measurements of the modulated reflectance signal can be made within a single period of the modulation cycle. In this way, the system allows the simultaneous measurement of the photoreflectance signal at all the wavelengths at which it is desired to measure it, in parallel by means of multiplexing the readout. The acquisition time for the entire spectrum is approximately that for a single wavelength.

Oversampling of the signal, that is to say, the acquisition of samples over a fraction of the period of the modulation, is essential to measure both the in-phase and quadrature components of the modulated signal, as well as the phase angle which they define. A phase stepping algorithm is employed to implement a phase sensitive sampling scheme. The overall algorithm comprises a multiplexed readout of each pixel of the photodetector array, performed multiple times per period of the modulation under the phase stepping algorithm. It must be noted that each successive pixel of the photodetector array is measured by the multiplexing part of the algorithm at a fixed phase increment out of step from the previous pixel, and the algorithm corrects for this fixed phase increment. An arbitrary phase angle can additionally be added to shift the modulated signal relative to the reference signal.

Therefore, in one embodiment, the detector array output is over-sampled by several times the modulation frequency and the data stream is processed using a phase-stepping algorithm in order to extract the full complex signal levels (in-phase and quadrature amplitudes and the phase angle which these define) from the modulation signal ($\Delta R$), simultaneously for all array elements (all wavelengths), as well as the corresponding time invariant array signal level. The electronics system comprises this phase-stepping algorithm and a system for rapidly reading the signal successively from each detector pixel in the array, in series, such that the time taken to read out the entire array of photodetectors is a fraction of the modulation period, and such that as a consequence, multiple measurements of the signal from each detector pixel in the array can be made within the period of the modulation. The electronics system comprises a driver circuit, and an analogue-to-digital converter, with in some embodiments, a signal processing or track-and-hole circuit to maintain the output signal from the driver circuit until it can be read by the analogue-to-digital converter.

The electronics system is capable of rapidly processing the large number of signal measurements thus made to calculate the amplitude of the ratio of the modulated reflectance signal to the time-invariant reflectance signal, at each wavelength.

This affords the possibility of measuring the entire photoreflectance spectrum of one location on a wafer in the time which prior art photoreflectance apparatus requires to measure the photoreflectance signal at that same location for just a single wavelength. The time saving and the increase in throughput due to this invention, is therefore of order of the number of wavelengths at which it is desired to make a measurement. This number of wavelengths at which the photoreflectance signal is measured in a spectrum at a single location on a sample is typically between 100 and 500 in most applications, so the potential time saving due to this invention is between 2 and 3 orders of magnitude. The system of the invention also eliminates moving parts from prior art systems, which require the scanning of a monochromator grating, and in doing so, greatly improves the spectrum-to-spectrum wavelength repeatability and the reliability of the measurement. Moreover, the use of an integrated photodetector array, as opposed to an array of discrete photodetectors, reduces the possibility of pixel-to-pixel quality variations.

The system and its method of operation measure the photoreflectance spectra of semiconductors using modulation spectroscopy, and determine from these photoreflectance spectra one or more of the following parameters: direct interband transition energies (bandgap energies), quantum well transition energies, electric field strengths of the in-built d.c. electric fields in certain semiconductors, carrier concentrations, and quantities determined indirectly from these, including: strain, alloy composition and lasing wavelength.

Referring also to FIG. 2, the following describes the system 1 in more detail.

Probe Beam Light Source 2

The probe beam light source 2 comprises a probe light source subsystem for producing a light beam having a broad spectrum of wavelengths, and optical components 16-18 for shaping the light beam and coupling it to the input probe beamsteering subsystem 3. These optical components may also include a bandpass filter in preferred embodiments of the invention, transmitting to the sample only those wavelengths of light for which it is desired to measure the modulated reflectance spectrum, so that the probe beam light intensity on the sample is minimised to avoid significant photovoltage effects.

Input Probe Beamsteering Subsystem 3

The input probe beamsteering subsystem 3 comprises optical components 19-22 for shaping a light beam 4, steering it, and coupling it to the sample 5.

Pump Light Source 11, Optical Components 12 and Modulator 14

The pump light source 11 produces a light beam having a single wavelength or a narrow spectrum of wavelengths, and the optical components 12 shape the light beam 13 and couple it to other subsystems. The wavelength of the light source is chosen such that the corresponding photon energy is greater than that of the bandgap of a semiconductor to be inspected, or is greater than the separation of two molecular electronic energy levels of a chemical substance to be inspected, or is otherwise sufficient in photon energy to cause the creation of photo-induced charge carriers in the sample material to be inspected. The pump beamsteering subsystem 12 has optical components for shaping a light beam, and steering it. It may comprise the pump beam optical intensity modulator 14 for modulating its amplitude or its direction and point of incidence on the sample material, and coupling it to the sample. The modulator 14 modulates the intensity of the light steered to the point of incidence of the pump beam on the sample, either by means of amplitude modulation or by means of alternating the position of incidence of the pump beam 15 on the sample from a position coincident with the point of incidence of the probe beam 4 on the sample 5, to a position in which the pump 15 and probe beam 4 areas of incidence do not wholly or partially coincide at the sample 5.

Output Probe Beam Subsystem 7

The output probe beam subsystem 7 comprises optical components 23-25 for coupling a light beam 6 reflected from a sample 5 to the dispersive system 8 such as a spectrograph 8.

Spectrograph 8 and Multi-Channel Detection System 9-10

The spectrograph 8, detector pixel array 9, and associated electronics system 10 comprising a signal processing system 26 and a computer 27, lie at the heart of the invention. A more detailed description of these components and their operation is provided below under the heading "Operation of the spectrograph and multi-channel detection system".

Sample Mounting Subsystem

A sample mounting subsystem is provided for holding a sample 5, and it may also move the sample 5 relative to the probe beam, to allow the acquisition of the modulated reflectance signal at multiple locations on the wafer. The sample 5 is horizontally mounted in preferred embodiments of the invention, and the sample mounting subsystem may have a means for moving the sample vertically up and down to place its surface in the vertical position corresponding to the optimum alignment of the light beam from the input probe beam subsystem 3 to the output probe beam subsystem 7 by reflection from the sample surface.

Assembly of the System Modules

The system comprises a mechanical assembly such that the beamsteering subsystems 3 and 7 are mounted with their optical axes at equal angles relative to the sample 5, which has a reflecting surface, such that the light beam from the input probe beam subsystem 3 is reflected from the sample into the optical path of the output probe beam subsystem 7.

The probe light source subsystem 2 is optically coupled to the input probe beam subsystem 3. The pump light source subsystem 11 is optically coupled to the pump beam optical subsystem 12.

The input probe beam subsystem 3 and the output probe beam subsystem 7 are mounted on the mechanical subsystem, such that their optical axes make equal angles relative to the line normal to the surface of a sample 5 which has a reflecting surface and is mounted on the sample mounting subsystem, such that the light beam from the input probe beam subsystem 3 is reflected from the sample 5 into the optical path of the output probe beam subsystem 7. The pump beam optical subsystem 11 is mounted on the mechanical subsystem, such that the pump beam, when not deflected or switched off by the modulator 14 is incident at the same position of the sample as the light beam from the probe beam 4, and for any angle of incidence of the probe beam on the sample, at least fully covers the probe beam spot area on the sample. The pump beam optical subsystem 13 may be mounted such that the angle of incidence of the pump beam is normal to the sample surface, or is at some other angle of incidence, in different embodiments of the invention, to allow other subsystems to be incorporated.

The dispersive system 8 is interposed between the output probe beam subsystem 7 and the detector array 9, which is mechanically coupled to the output port of the dispersive system 8. The detector array 9 is connected to the electronic means 26 for recording the electrical signal.

The computer subsystem 27 is used to control the functions of the system 1.

A synchronous amplitude modulator may be inserted in the probe beam path, to make a double modulation system, in conjunction with a more complex phase stepping acquisition algorithm.

The system also comprises an electrical power subsystem for providing mains and low voltage electrical power.

Optical Path of the Pump and Probe Beams Through the Apparatus

The optical path through the apparatus of FIG. 2 is as follows:

The probe beam light source subsystem 2 produces a broad spectrum light beam which is coupled by a pair of lenses of suitable f-number into a fibre optic of the input optical probe beam subsystem 3. The spectrum of the light beam may be reduced to a narrower spectral extent if desired by interposing a filter between the light source 16 and the end of the input optical probe beam subsystem 3.

The lens 20 is the objective lens of a Galilean telescope, the eyepiece lens 21 of which is placed such that a parallel probe beam 4 of demagnified diameter is produced at the output of lens 21, and is focused using a high-f-number lens 22 onto a sample material 5.

The modulation system 14 modulates the pump beam 13 into an amplitude or spatially modulated pump beam 15, which is directed to an area of coincidence with the area of incidence of the probe beam 4 on the sample 5.

The lenses 23 and 25 and the mirror 24 couple the beam to a spectrograph 8. The lens 25 has a suitable f-number compared to the f-number of the spectrograph 8 such that it causes the light from lens 25 to fill most of the width of the grating or other dispersive optical element contained within the spectrograph 8 in order to obtain a near-optimum spectral resolution from the spectrograph 8.

A notch filter (or alternatively a long-pass filter) can be interposed between the sample 5 and the spectrograph 8 if required to reject large amounts of scattered modulated pump light collected by the optical system from the sample 5. The filter preferably has negligible transmission at the wavelength of the pump light source 11 but high transmission at least over a wide spectrum of wavelengths longer than the wavelength of the pump light source 11 and extending over the wavelengths at which the modulated reflectance of the sample 5 is to be measured.

Operation of the Spectrograph and Multi-channel Detection System

The detector subsystem 9 comprises an array of detectors, namely detector pixels 9, for detecting light from the reflected probe beam 7. Each pixel is an integrating photodetector. The spectrograph 8 disperses the light from the reflected probe beam 7 into its constituent wavelengths to provide dispersed beams such that only a different narrow range of wavelengths of the constituent wavelengths of the reflected probe beam light are transmitted onto each pixel, and such that the entire array of detector pixels 9 detects light over a broader wavelength range of the probe beam.

The electronic subsystem 10 comprises an electronic signal processing system 26 and a computer system 27. The computer subsystem 27 is used for control of the system and for processing of recorded data. The electronic signal processing system 26 is capable of making a measurement from each detector pixel in the array of detector pixels 9, either simultaneously or in sequence, such that the signals from the entire array of detector pixels 9 are measured in a time which is a fraction of the period of the modulation of the pump beam 14, and is capable of repeating this reading of the signal from the entire array, periodically, multiple times during each modulation period and for multiple cycles as programmed by the computer system 27. The computer system 27 is capable of processing the data recorded by the electronic signal processing system 26 in order to determine the photoreflectance spectrum of the sample at the measurement location defined by the area of incidence of the probe beam during the data recording.

Figure 3:
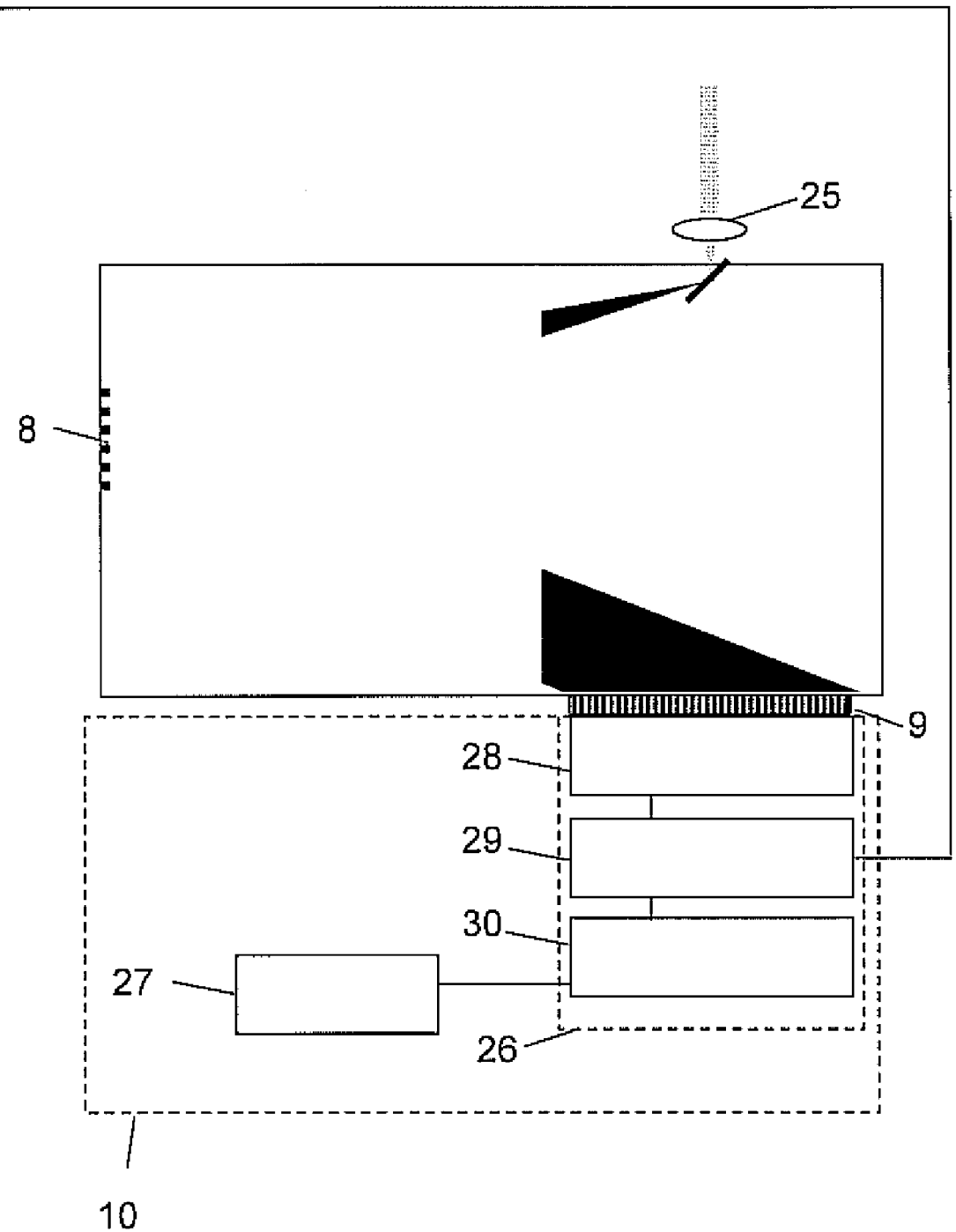
FIG. 3 is a diagram of a spectrograph, a detector, an associated detector driver, and signal processing and readout electronics according to embodiments.

Referring also to FIG. 3, the following describes the electronic signal processing system 26 in more detail. The electronic signal processing system 26 comprises a driver and pulse generator circuit 28 routing power to and signals from the array of detector pixels 9, a track and hold circuit 29, and an analogue-to-digital converter circuit 30, which are inserted within the computer system 27. In other systems of the invention, the driver and pulse generator circuit 28, the track and hold circuit 29, and analogue-to-digital converter circuit 30 may be integrated into a single electronic signal processing system, and this electronic signal processing system may also include a programmable logic controller, which may comprise a programmable gate array, as well as signal accumulation electronic circuits which are capable of electronic summing multiple reflectance spectra read out from the detector array 9.

The detector array 9 is connected to the driver and pulse generator circuit 28 routing power to and signals, including clock pulses, from it, and output signals from the detector array via driver and pulse generator circuit 28 are routed to the track and hold circuit 29, which functions to extend the length of the output pulses from the detector array 9 via its associated driver and pulse generator circuit 28 to make them compatible with the readout rate of the analogue-to-digital converter circuit 30, to which the signals are passed from the track and hold circuit 29.

It is envisages that, if the output pulses from the detector array 9 via its associated driver and pulse generator circuit 28 are already compatible with the readout rate of the analogue-to-digital converter circuit 30, no track and hold circuit 29 is required. The photodetector array 9 may be operated in either voltage mode or current mode, with an appropriate choice of driver board 28. In preferred methods of the invention, the photodetector array 9 is operated in current mode.

Timing of the Measurements from and Operation of the Photodetector Array

Each detector pixel detects the optical signal from a small subset range of wavelengths from the spectrum of the reflected probe beam light which has been dispersed by the spectrograph 8. This light generates charge in the photodetector, with a quantum efficiency $\eta$, which partially or completely fills a quantum well in the integrating photodetector pixel. Each integrating photodetector pixel has a well capacity defined as a charge Q, after which the detector ceases to integrate charge and must be read out by an electronic circuit. The signal in the detector comprises integrated electrical charge, due to both a time-invariant signal, corresponding to the unmodulated reflectance signal R, and a small time-varying periodic signal, corresponding to the modulated reflectance signal $\Delta R$, averaged over this narrow range of wavelengths. There will also be some charge due to noise in any real detector system, and the limiting amount of this noise is the shot noise level, given as the square root of the number of photons collected in the detector over a fixed time interval. The charge Q represents a number of electrons $X=Q/e$ where e is the charge on the electron, and the shot noise inherent in this number of electrons is $X^{0.5}$. Thus for a resolution of a low amplitude modulated signal such that the noise level is 1 part per million (1 ppm), $10^{12}$ electrons must be accumulated so that the shot noise level is $10^6$ electrons, or one-millionth of the charge accumulated. In practical systems of the invention, there will exist random noise contributions from sources other than the detector, including shot noise in the optical source from which the detected probe beam is derived, and in practice, several times this amount of charge may require to be accumulated to overcome the multiple sources of random noise.

In most integrating photodetectors, the quantum well capacity severely limits the number of electrons which can be accumulated before a readout is required, such that a large number of sample readouts must be accumulated to achieve shot noise levels below 10 ppm.

Figure 4:
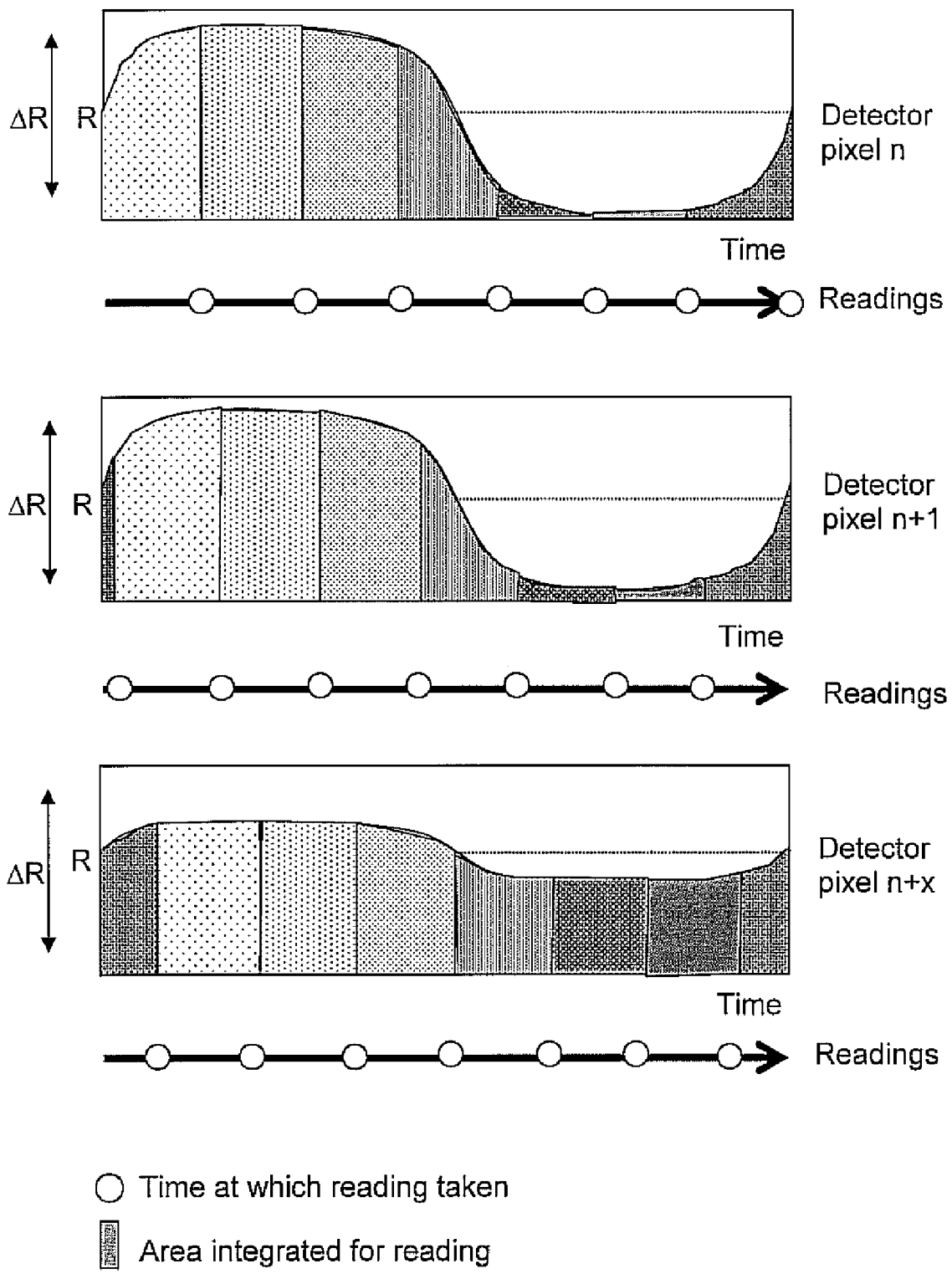
FIG. 4 is a timing diagram showing the sequence of reading of the detector pixels for a case of a non-sine wave modulated signal for a single period of the modulation according to embodiments.
Figure 5:
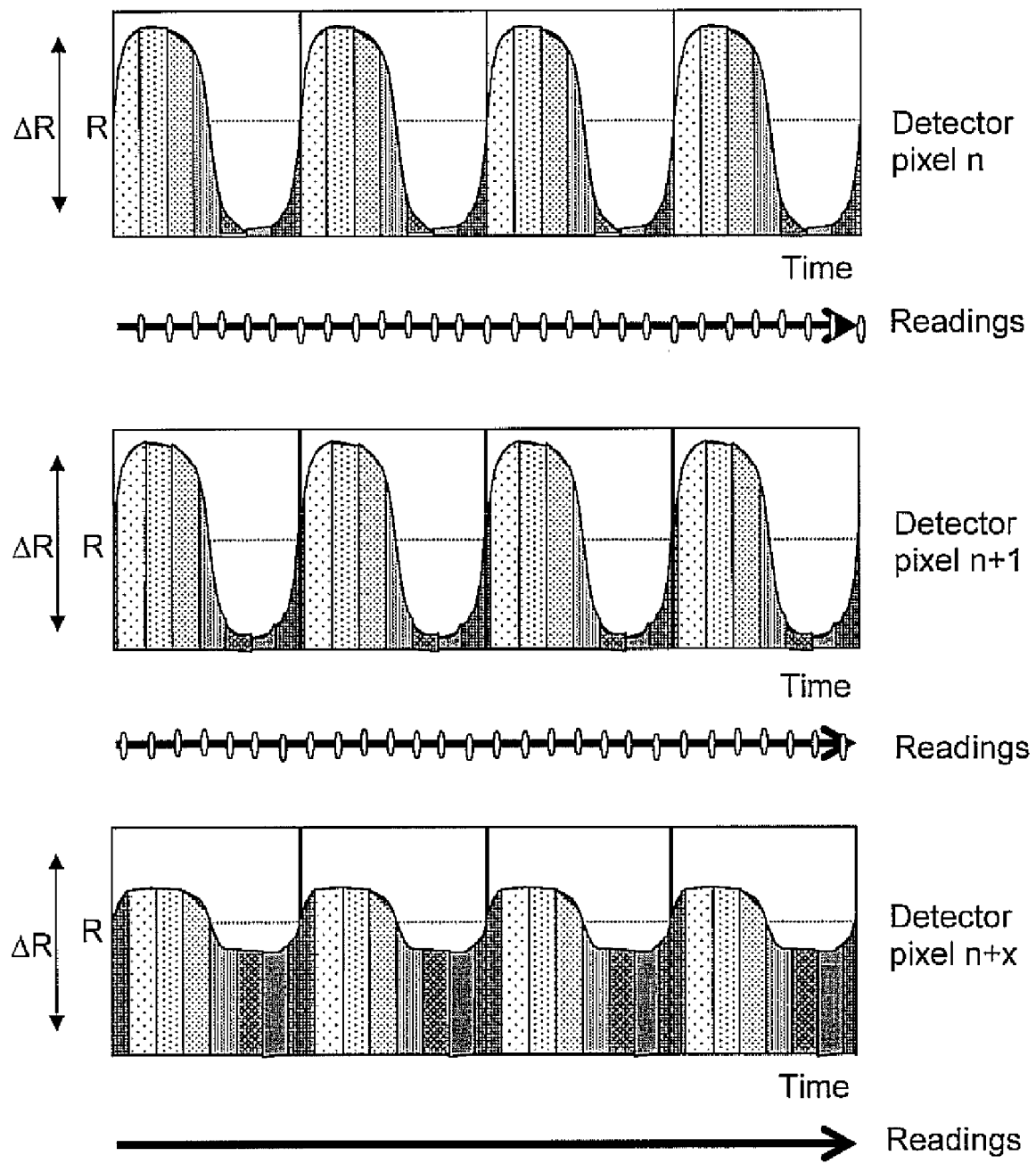
FIG. 5 is a timing diagram showing the sequence of reading of the detector pixels for a case of a non-sine wave modulated signal for four successive periods of the modulation according to embodiments.

The sequence and timing of the measurements will be better understood by reference to the timing diagrams in FIGS. 4 and 5.

FIGS. 4 and 5 each consist of three subfigures. Each subfigure refers to a single pixel of the detector array. The horizontal axis represents time. Only one period over which $\Delta R$ is modulated is shown in FIG. 4. More than one period over which $\Delta R$ is modulated is shown in FIG. 5. The upper part of each subfigure represents the intensity of light falling on each of the pixels over a period of time. If we consider just the unmodulated reflectance signal R and the modulated reflectance signal ΔR, the signal in an ideal noise-free detector would be of periodically varying amplitude about the value R, with time, as shown in the diagrams in FIG. 4. Note that in practice this is a very small modulation ΔR on a relatively large background reference signal R. The lower part of each subfigure represents the magnitude of the signal read from the pixel in question (a different pixel for each subfigure) and the point in time at which this signal is acquired. Note that the magnitude of the pixel reading is proportional to the total intensity of light falling on that pixel since the pixel was last read.

The amplitude of both the unmodulated reflectance signal R and the modulated reflectance signal ΔR will in general be different for each detector pixel, as shown in the lower panels of FIGS. 4 and 5, due to the spectral variations in the R and ΔR. The measurement of the modulated reflectance at a single wavelength requires that enough samples of the modulated reflectance signal ΔR are made within a single period of the modulation to allow the calculation of the amplitude of the modulated reflectance signal ΔR and its phase angle with respect to the reference signal, as well as making a measurement of the unmodulated reflectance signal R, from one detector pixel. This measurement must be carried out for all the detector pixels in order to obtain the modulated reflectance spectrum.

Signals are recorded from the detector array 9 in the following manner. The signal from each detector in the array is read in sequence by the digital signal processing subsystem 26 and recorded. The process is repeated a multiple M of times during a time interval equal to the period of the modulation of the pump beam. The modulation system of the pump beam 14 is electrically connected to the electronic system 26 to ensure that the readings are taken in the correct timing interval.

In order to recover the amplitude and phase of a modulated signal at a single, known, reference frequency, a phase stepping demodulation algorithm is employed using an analogue-to-digital converter 30 to oversample the entire detector array 9 by a multiple M of the modulation frequency of the pump beam modulator. M multiple measurements must be made from each pixel during the period of the modulated signal, such that every pixel is read in sequence during each fractional period. The timing of the measurements from each pixel is itself successively incremented by a small fraction of these fractional periods. We can therefore define the period fraction as 1/M.

The sequence and timing of the measurements will be better understood by reference to the timing diagrams in FIG. 4, for the general case of a non-sinusoidally modulated signal, such as that practically obtained by mechanically chopping a light beam using a rotating wheel with apertures, or resulting from the physical processes underlying the response of a semiconductor to a modulated pump light beam, whether that pump beam is sinusoidally or non-sinusoidally modulated.

The timing of the pixel readouts is controlled by the electronic subsystem 26, and this ensures that there are an exact integer number of signal readings per pixel for each modulation cycle of ΔR. In this way, if there are M readings per pixel per cycle, then every Mth reading per pixel will be of the same portion of the modulation cycle ΔR. In this way a number of readings for each part of the modulation cycle can be acquired and averaged, and it is this mechanism by which a very small modulation ΔR can be detected on a large time-invariant background reading R at a fixed modulation frequency.

Therefore, the process of reading in sequence the signals from all the pixels in the detector is repeated a multiple M of times during a time interval equal to the period of the modulation of the pump beam. In the case of a modulated waveform which is non-sinusoidal, more than four measurements must be made in order to correctly measure the amplitude and phase of the modulated signal. In the example shown in the timing diagram in FIG. 4, seven readings are taken for each cycle of the modulated reference signal. The signal from each pixel is proportional to the product of the light intensity falling on that pixel and the integration time, where the integration time in this sense refers to the time period between the pixel having last been reset and the time at which the signal is acquired. Each pixel is reset in turn immediately after its signal has been acquired. In this case, the integration time is constant for all the pixels of the detector, and there is only a very short period of time (between the pixel signal being acquired and the point in time at which the pixel is reset) that the light falling on each pixel is not contributing to the signal that is output from that pixel. The acquisition of the data from the array of detectors is thus performed in multiplexed readout manner which simultaneously measures the modulated signal from all pixels in the detector array.

In this case of a non-sinusoidally modulated signal, seven readings during the period of the signal are shown. The period fraction is therefore one-seventh. During each one-seventh period, each one of N integrating photodetector pixels must be read out once, and this operation is performed sequentially for each successive detector pixel.

In preferred methods of the invention a small, odd number of readings per period of the signal, such as five or seven readings per period, has been found to be sufficient to reconstruct the in-phase and quadrature signals and the phase angle which these signals define, with relatively low noise levels. It has been discovered that square wave mixing leads to larger phase dependent errors (which are in any case correctable within the algorithm), especially for the case of 4 readings per period, and in general for even numbers of readings per period, so that it is desirable to select an odd number of readings per period.

If the modulation frequency is $f_{mod}$, then the readout frequency $f_{readout}$ which must be achieved to measure both the in-phase and quadrature signals and the phase angle which these signals define, is therefore given by:

$$f_{readout} = M\, Nf_{mod} \qquad 1$$

The speed limitation of the photoreflectance signal acquisition system is practically defined by the maximum readout frequency $f_{readout}$ of the detector array. For an N=512 pixel array, capable of being read out at a maximum frequency of $f_{readout}$=500 kHz, then for M=7 readings of the entire array per modulation period $1/f_{mod}$, the maximum modulation frequency (to the nearest whole number) is $f_{mod}$=139 Hz. This frequency is sufficiently high for photoreflectance spectroscopy.

Now considering a typical detector pixel quantum efficiency of η=50%, a well charge capacity of Q=50 pC, giving a number of electrons of $n_e$=3.13×10$^8$ to fill the well, and an algorithm to readout the detector at approximately 75% of full well at most, to ensure that saturation effects are avoided, reducing $n_e$ to 2.34×10$^8$ electrons. (The number of photons required to produce this number of electrons is $n_p$ 6×10$^8$ photons). Shot noise is however dependent on the number of electrons, not photons. Provided that the light intensity is sufficient to compensate for the less than unity quantum efficiency, then in order to have a shot noise level of 6.53 ppm, or 1.53×10$^5$ electrons, the number of electrons collected must be $n_e$=2.34×10$^{10}$ electrons, or 100 samples of the detector at each period fraction. The number of samples S of the detector increases or decreases from this as the square of the required shot noise level.

For example, a shot noise level of 2.176 ppm, in this particular example of the invention, would require $3^2 \times 100$ samples, or 900 samples of the detector at each period fraction. Therefore, 900 periods of the modulation must be sampled in this case of a shot noise level of 2.176 ppm, and the time taken is 900/139 seconds, or 6.47 seconds. If a shot noise level of 3 ppm can be accepted, the measurement time for the entire spectrum falls to 3.41 seconds.

These examples of measurement times serve to illustrate the exceptional speed with which a full modulated reflectance spectrum can be measured using this invention, consistent with a high signal to noise ratio. In cases where the spectral resolution per detector pixel is finer than required, then multiples of pixels can be combined together, reducing further the time required to accumulate sufficient charge to meet a given shot noise level, and making the system of the invention even faster. A judicious choice of the combination of the spectrograph dispersing element, usually a diffraction grating, and the photodetector array, can achieve this result.

Phase Stepping Demodulation Algorithm

Figure 6:
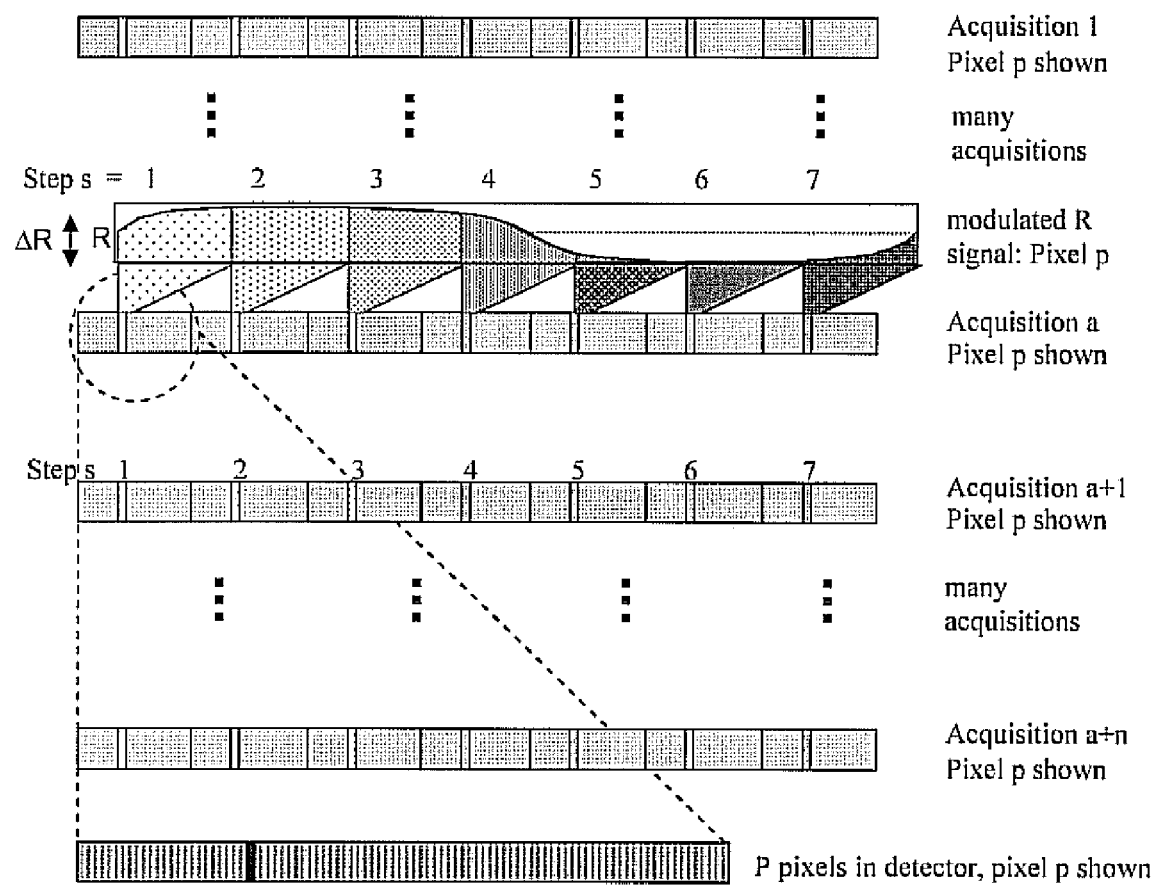
FIG. 6 is a timing diagram showing the sequence of reading of the detector pixels and operation of a phase stepping demodulation algorithm for a case of a non-sine wave modulated signal for a single period of the modulation according to embodiments.

The phase stepping demodulation algorithm may be described in mathematical terms with reference to FIGS. 4 to 6.

The method requires that a multiplicity of measurements (called the oversampling number of steps S) of the raw reflected probe beam optical signal on the photodetector is made during each modulation cycle. Errors are dramatically reduced in the case of a periodic but non-sinusoidal modulation of the reflection signal if the value of S is an odd number. In the standard operating conditions, S=7.

The measurement method consists in the performance of a readout measurement of a signal V from each pixel p, S times per period of the modulation of the pump beam. Each time during the period of the modulation at which a measurement is made is referred to as a step s. The measurement method requires that a large number of repeated acquisitions a of the set of S step measurements from each pixel p be made, to reduce random noise including shot noise to an acceptable level below the level of the modulated reflectance signal.

Let $V_{pixel(p)acquisition(a)step(s)}$ be the signal from the detector pixel p, during step s of acquisition a.

The computer system, if it receives the signals individually from the detection electronics system, or else the accumulation electronics circuit if one is employed, sums the $N_{acquisitions}$ sample signals $V_{pixel(p)acquisition(a)step(s)}$ which correspond to the same step s of the modulation period from each pixel p, according to equation 2, to obtain a result $R_{pixel(p)step(s)}$ which is proportional to the light of a specific wavelength which is directed onto pixel p of the detector, during a specific fraction of the period of the modulation of the pump beam and therefore of the reflectance of the sample. The process is repeated for step s of the modulation period, and for each pixel p of the detector array, or for each detector p, in embodiments where the system employs a multiplicity of detectors.

$$R_{pixel(p)step(s)} = \frac{\sum_{a=1}^{N_{acquisitions}} V_{pixel(p)acquisition(a)step(s)}}{N_{acquisitions}} \qquad 2$$

This gives a set of s values of the reflected probe beam signal R from the sample for each pixel p, one for each fraction of the period of the modulation of the pump beam and therefore of the reflectance of the sample.

The unmodulated R signal is then determined by a summation of the s values of the reflected probe beam signal R from the sample for each pixel p, for each fraction of the period of the modulation of the reflectance of the sample, according to equation 3.

$$R_{pixel(p)} = \frac{\sum_{s=1}^{S_{steps}} R_{pixel(p)step(s)}}{S_{steps}} \qquad 3$$

Within set of s values of the reflected probe beam signal R from the sample for each pixel p, one for each fraction of the period of the modulation of the pump beam and therefore of the reflectance of the sample, there is contained a modulated reflectance signal $\Delta R$. The modulated reflectance signal $\Delta R$ comprises a component of the signal $\Delta R_{in-phase}$ which is in-phase with the reference signal which is used to modulate the pump beam or which is derived from the modulator, and a component of the signal $\Delta R_{quadrature}$ which is in quadrature with the said reference signal. The component of the signal $\Delta R_{in-phase}$ which is in-phase with the reference signal, is demodulated from the R signal by first implementing the transform algorithm expressed in equation 4, which may be expressed in simpler terms, requiring fewer computing steps by relying on the result of equation 2, in equation 5.

$$Transf_{in-phase-pixel(p)step(s)} = \qquad 4$$
$$\frac{\sum_{n=1}^{N_{acquisitions}} V_{pixel(p)acquisitions(a)step(s)} \sin(\Phi_{pixel(p)step(s)})}{N_{acquisitions}}$$

$$Transf_{in-phase-pixel(p)step(s)} = R_{pixel(p)step(s)} \sin(\Phi_{pixel(p)step(s)}) \qquad 5$$

The demodulation phase angle $\Phi_{pixel(p)step(s)}$ is determined from equation 6, where there are $S_{steps}$ steps of oversampling per modulation period.

$$\Phi_{pixel(p)step(s)} = \phi_{phaseadjust} + \frac{2\pi\left(s - \frac{1}{2}\right)}{S_{steps}} + \frac{(p-1)}{P_{pixels}} \frac{2\pi}{S_{steps}} \qquad 6$$

In equation 6, the first term is an arbitrary phase adjustment angle $\phi_{phaseadjust}$, which may be added to the demodulation phase angle in order, for example, to render the entire modulated reflectance signal in-phase with the reference signal. The second term represents a phase angle corresponding to exactly the number of fractional periods from the start of a modulation period to exactly half way through the $s^{th}$ step fractional period. The sequence of readouts of the detector signal is such that this phase angle is added for each step. The third term in equation 6 represents a pixel phase angle, which is an additional angle, corresponding to the fraction of 1/s of a fractional modulation period, which elapses between the time at which the detector signal is read out from pixel 1 and the time at which the detector signal is read out from pixel p. Failure to make the corrections represented by the second and third terms in equation 6 will cause the demodulation algorithm to operate incorrectly and to give incorrect or erratic results or to fail completely to demodulate the modulated signal from the reflectance spectra.

The component of the signal $\Delta R_{in\text{-}phase}$ which is in-phase with the reference signal, is then demodulated from the R signal by performing the summation in equation 7.

$$(\Delta R)_{in\text{-}phase\text{-}pixel(p)} = \frac{\sum_{s=1}^{S_{steps}} Transf_{in\text{-}phase\text{-}pixel(p)step(s)}}{S_{steps}} \quad 7$$

The component of the signal $\Delta R_{quadrature}$ which is in quadrature with the said reference signal is then demodulated from the R signal by first implementing the transform algorithm expressed in equation 8, which may be expressed in simpler terms, requiring fewer computing steps by relying on the result of equation 2, in equation 9

$$Transf_{quadrature\text{-}pixel(p)step(s)} = \quad 8$$
$$\frac{\sum_{n=1}^{N_{acquisitions}} V_{pixel(p)acquisition(a)step(s)} \cos(\Phi_{pixel(p)step(s)})}{N_{acquisitions}}$$

$$Transf_{in\text{-}phase\text{-}pixel(p)step(s)} = R_{pixel(p)step(s)} \cos(\Phi_{pixel(p)step(s)}) \quad 9$$

The component of the signal $\Delta R_{quadrature}$ which is in quadrature with the reference signal, is then demodulated from the R signal by performing the summation in equation 10.

$$(\Delta R)_{quadrature\text{-}pixel(p)} = \frac{\sum_{s=1}^{S_{steps}} Trans_{quadrature\text{-}pixel(p)step(s)}}{S_{steps}} \quad 10$$

The component of the photoreflectance signal which is in-phase with the reference signal, is then determined from equation 11, derived from equations 3 and 7.

$$PR_{in\text{-}phase\text{-}pixel(p)} = \frac{\Delta R_{in\text{-}phase\text{-}pixel(p)}}{P_{pixel(p)}} \quad 11$$

The component of the photoreflectance signal which is in quadrature with the reference signal, is then determined from equation 12, derived from equations 3 and 10.

$$PR_{quadrature\text{-}pixel(p)} = \frac{\Delta R_{quadrature\text{-}pixel(p)}}{R_{pixel(p)}} \quad 12$$

The magnitude of the photoreflectance signal is then determined from equation 13, derived from equations 3 and 7.

$$PR_{magnitude\text{-}pixel(p)} = \sqrt{\frac{(\Delta R_{in\text{-}phase\text{-}pixel(p)})^2 + (\Delta R_{quadrature\text{-}pixel(p)})^2}{R_{pixel(p)}}} \quad 13$$

The operation of the detection system so described is fundamentally different from that of a lock-in amplifier, in that the concept of a time constant characterising the charging of a capacitive circuit does not exist. The system is instead a clocked multiple sampling readout system of an array of quantum well integrating photodetectors, under the control of a phase stepping algorithm which is itself driven by the modulation reference frequency. The basis for the time of measurement depends on the number of samples required, which is solely related to the desired level of shot noise.

In some other embodiments of the invention, in which the particular type of detector or electronic system requires it, the reading is made while the light to the detector is momentarily blocked at the end of some period during which the detector has been illuminated, using a programmably or electrically controlled device for periodically blocking the probe light beam may be inserted at some point between the light source for the probe beam 2 and the detector array 9.

The data thus recorded is processed in either the electronic subsystem 26 or in the computer system 27 or both, and from it may be determined the following raw data parameters:

periodic signal at the modulation frequency for each wavelength corresponding to each detector array pixel, and time-invariant signal for each wavelength corresponding to each detector array pixel, In addition, in some preferred embodiments of the invention it may determine the following parameters:

periodic signal at the modulation frequency in-phase with the modulation of the pump beam for each wavelength corresponding to each detector array pixel, periodic signal at the modulation frequency quadrature with the modulation of the pump beam for each wavelength corresponding to each detector array pixel, phase angle of periodic signal at the modulation frequency for each wavelength corresponding to each detector array pixel, and magnitude (resultant of in-phase and quadrature) periodic signals for each wavelength corresponding to each detector array pixel.

The result of the measurement is expressed as the dimensionless quantity $\Delta R/R$, known as the photoreflectance signal. The measurement of the spectrum of $\Delta R/R$ over a desired range of wavelengths is achieved simultaneously (which can be by means of a multiplexing detector readout method as described above) at multiple wavelengths by means of the parallel signal acquisition system. The following parameters may be determined from the said raw data parameters:

photoreflectance signal (ratio $\Delta R/R$ of modulated reflectance signal to unmodulated reflectance signal) for each wavelength corresponding to each detector array pixel, and reflectance signal R (unmodulated reflectance signal) for each wavelength corresponding to each detector array pixel, and in addition, in some preferred embodiments of the invention:

photoreflectance signal $\Delta R/R$ in-phase with the modulation of the pump beam for each wavelength corresponding to each detector array pixel, photoreflectance signal $\Delta R/R$ quadrature with the modulation of the pump beam for each wavelength corresponding to each detector array pixel, phase angle of photoreflectance signal $\Delta R/R$ for each wavelength corresponding to each detector array pixel, and magnitude (resultant of in-phase and quadrature photoreflectance signals) signal ΔR/R for each wavelength corresponding to each detector array pixel.

Measurement of Photoreflectance Spectra Using the System of the Invention

In use, the system performs as follows:

(a) the delivery of a light beam called the "probe beam" to a sample, its specular reflection from the sample, and the steering of the reflected light beam called the "reflected probe beam" through a spectrally dispersive optical element or system, such as a spectrograph, onto an array of regularly spaced photodetectors, (b) the periodic illumination of at least all of the area of incidence of the probe beam on the sample by means of the pump beam at a modulation frequency F, and with light of a photon energy which in the case of a semiconductor is greater than the bandgap energy of the semiconductor, and in the case of other sample materials which is of sufficient energy to photogenerate charge carriers in the material, (c) simultaneous detection of the time-invariant reflected probe beam intensity denoted R and any amplitude modulated time-variant component of the reflected probe beam intensity denoted ΔR at the amplitude modulation frequency F of the pump laser beam, and simultaneous (which may include multiplexed) recording of data from the detector array, such that the ratio denoted ΔR/R can be determined as a spectrum over a range of wavelengths.

(d) analyzis of the photoreflectance spectrum ΔR/R as a function of the probe beam photon energy in order to determine the transition energy of one or more of the electronic transitions in the semiconductor which causes the appearance of the photoreflectance lineshape signals in the photoreflectance spectrum. These transition energies may also be used to determine strain and/or alloy mole fraction in at least one semiconductor layer in the sample, or to determine a quantum well transition energy. The broadening parameter, signal phase and/or amplitude or the PR signal may also be determined if required. Analyzes may also be performed to determine the d.c. electric field strength in or near the interface of one or more of the semiconductor layers present in the sample.

The probe beam 4 may be delivered to the sample as a filtered beam, having a narrower range of wavelengths than the light source 2 from which it is derived, in order to expose the sample to the minimum possible intensity of light in the part of the modulation cycle in which the modulated pump beam 15 is not incident on the area of incidence of the probe beam on the sample, in order to avoid photovoltage effects.

The photoreflectance spectrum ΔR/R may be rapidly measured at a multiplicity of locations on the sample 5 by means of this invention, in embodiments in which a means is provided of moving the sample in its own plane, laterally, relative to the probe and pump beam area of incidence on the sample 5.

Analyzis of the Photoreflectance Spectrum Recorded by the System

Referring to FIG. 4, signals ΔR detected from each pixel of the detector array 9 are shown, in which the sample is biaxially strained silicon. It is noted that the ΔR is typically several orders of magnitude smaller than the R signal and is of a different signal amplitude in general in each pixel of the detector array; the graph of ΔR being shown on an expanded scale for clarity. The lower panel shows behaviour of the modulated reflectance signal ratio ΔR/R with spectral position (expressed in Photon Energy) in the region of the direct bandgap energy ($E_g$) of a semiconductor.

Figure 7:
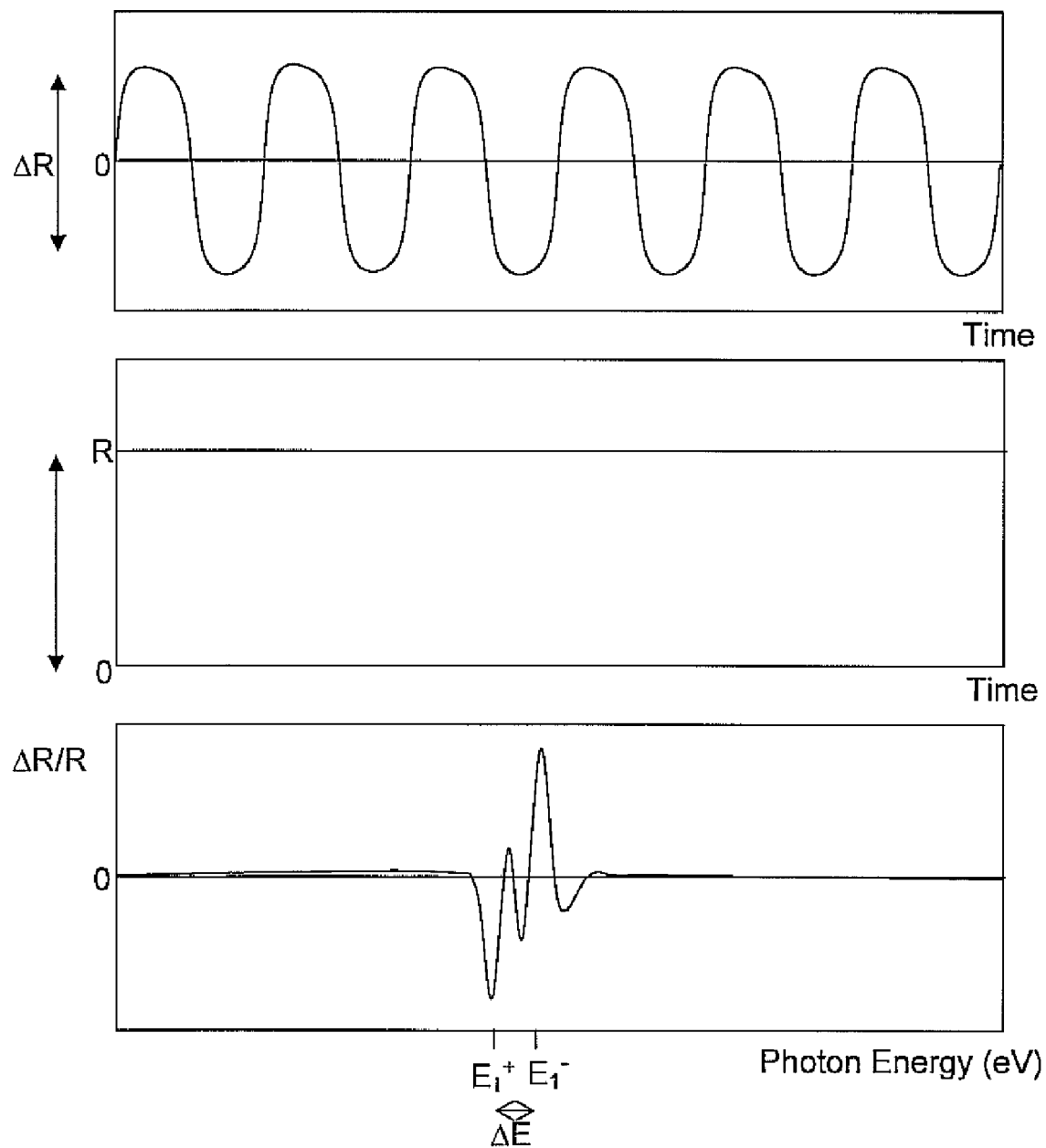
FIG. 7 is a plot of reflectance with time, a plot of modulated reflectance signals with time, and a photoreflectance spectrum for biaxially strained silicon according to embodiments.
Figure 8:
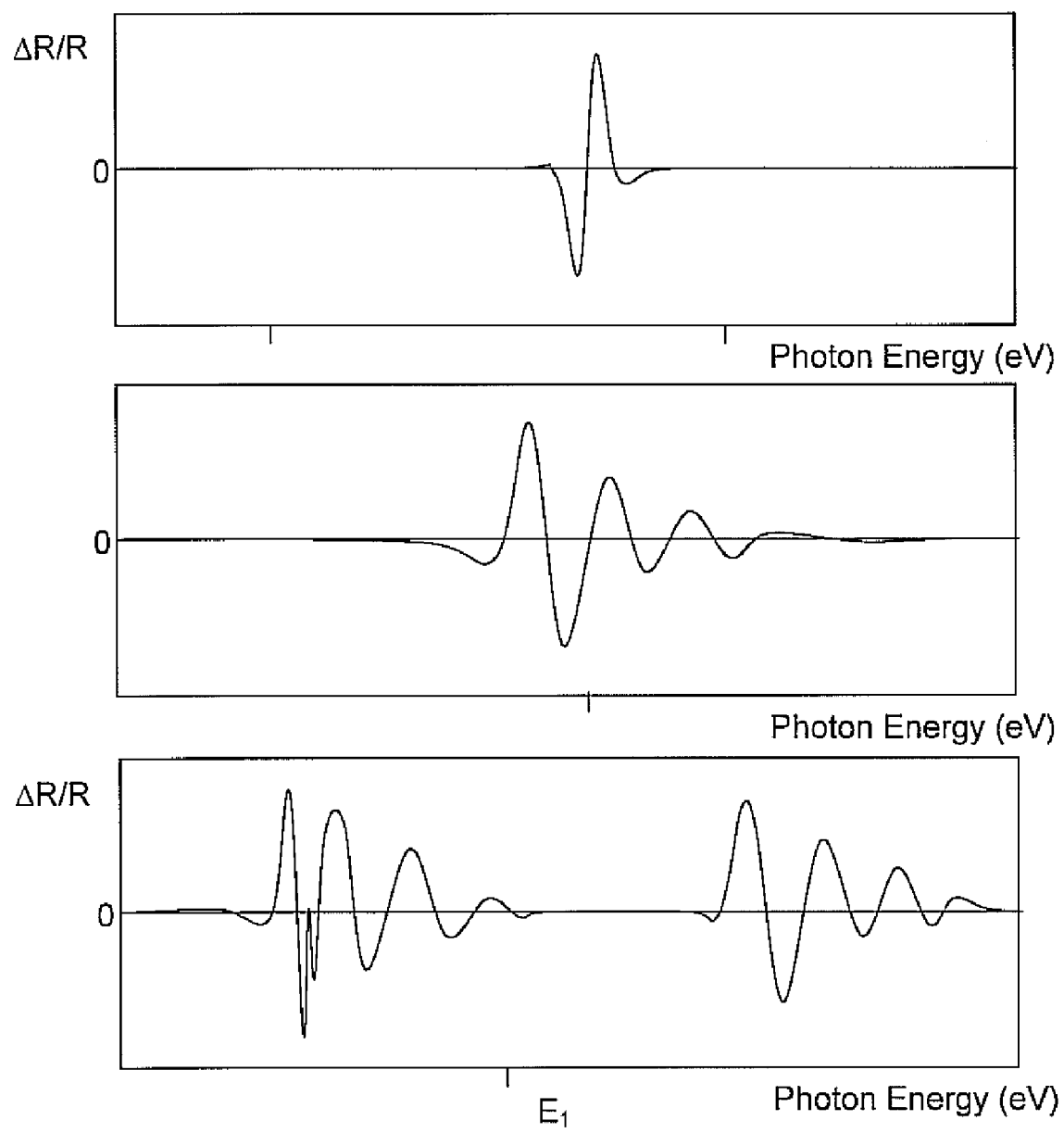
FIG. 8 is a set of plots of other photoreflectance spectra according to embodiments.

The relative amplitudes of the ΔR and R signals in each detector generally vary from detector to detector, as both ΔR and R exhibit spectral dependence. The waveform of the modulated reflectance is always periodic, and is in general more complex than a single sine wave. A typical modulated signal comprising a deformed square-wave is shown in FIG. 7, top panel. Further examples of in-phase photoreflectance spectra are shown in FIG. 8, the examples being of photoreflectance spectra ΔR/R as a function of photon energy E, measured by means of the invention. The upper panel shows one typical behaviour of the modulated reflectance signal ratio ΔR/R with spectral position (expressed in Photon Energy) in the region of the direct bandgap energy ($E_g$) of a semiconductor, when the electro-optic energy is less than the broadening parameter for the critical point transition in the semiconductor giving rise to the photoreflectance signal. The middle panel shows another typical behaviour of the modulated reflectance signal ratio ΔR/R with spectral position (expressed in Photon Energy) in the region of the direct bandgap energy ($E_g$) of a semiconductor, when the electro-optic energy is greater than the broadening parameter for the critical point transition in the semiconductor giving rise to the photoreflectance signal. The lower panel shows how the invention may be used to record photoreflectance lineshape spectra from two different spectral ranges, whether successive or separated by a spectral range in which no signal is recorded, and to combine them in a single spectrum, by means of changing the spectrograph output wavelength range after recording the photoreflectance lineshape spectrum in the first spectral range one typical behaviour of the modulated reflectance signal ratio ΔR/R with spectral position (expressed in Photon Energy) in the region of the direct bandgap energy ($E_g$) of a semiconductor. The spectrum shown is typical of that from a heterojunction bipolar transistor epitaxial wafer.

A part of the photoreflectance spectrum, within which the photoreflectance signal varies in magnitude at different probe beam photon energies, may be referred to as being a photoreflectance lineshape or as comprising one or more photoreflectance lineshapes. The photoreflectance spectrum comprises one or more, either separate or superimposed, photoreflectance lineshape components.

The analyzis of a photoreflectance spectrum comprising one or more of these types of photoreflectance lineshapes consists in the calculation of the theoretical photoreflectance spectrum obtained by the summation of one or more components represented by expressions of the general types recited in equation 2, and adjusting parameters within these expressions 2 using a regression fitting program, such as that of Levenberg and Marquardt, to minimize the error between the theoretically calculated photoreflectance spectrum and the measured photoreflectance spectrum. The parameters required in these expressions for the minimised error are accepted as the material parameters, and specifically in this case, the values of the transition energy $E_g$ for each component, as well as the amplitude, A, broadening parameter Γ, and phase θ, and where Franz-Keldysh oscillations are exhibited, the electro-optic energy and electric field in the semiconductor can be determined by this fitting procedure, given a knowledge of the effective mass for the electrons in the band.

An exception is the linear analyzis method for photoreflectance lineshapes exhibiting Franz-Keldysh oscillations, which does not require a regression fit to the lineshape, but to the straight line graph derived from analyzis of its peak and trough and/or zero point spectral positions.

The ΔR/R spectrum, of a photoreflectance spectrum or one or more photoreflectance lineshape components of a photoreflectance spectrum may fitted to or otherwise analyzed using one of a number of well-known formalisms describing the physical origins of the features of the spectrum. In cases where the semiconductor has a low internal electric field insufficient to cause the electro-optic energy to exceed the lineshape broadening energy parameter, these photoreflectance lineshape components are generally found to conform to the formalism of Aspnes known as the third derivative function form TDFF or "low-field" photoreflectance lineshape. This models the case of the photoreflectance effect in which any d.c. electric fields which are in-built in the semiconductor are insufficient to produce practically measurable Franz-Keldysh effects in the photoreflectance spectrum. This formalism of Aspnes is a derivative with respect to photon energy of a Lorenztian lineshape, the index m being selected differently with respect to the dimensionality of the direct interband transition in the Brillouin zone, and the photoreflectance spectrum ΔR/R(E) due to a single photoreflectance lineshape component of this type is represented by the expression 1. Other formalisms based on the electro-optic functions as represented by Airy Functions and their derivatives, or by approximations thereof, are appropriate when d.c. electric fields which are in-built in the semiconductor are sufficient to produce practically measurable Franz-Keldysh effects in the photoreflectance spectrum.

Among these formalisms and expressions may be the following:

The Third Derivative Functional Form (TDFF) due to Aspnes. This formalism of Aspnes is a derivative with respect to photon energy of a Lorentzian lineshape, the index m being selected differently with respect to the dimensionality of the direct interband transition in the Brillouin zone, and the photoreflectance spectrum ΔR/R (E) due to a single photoreflectance lineshape component of this type is represented by the expression 1 below.

The First Derivative Functional Form (FDFF) due to Aspnes, in which the index m in expression 2 is changed Other expressions of the general form of a Lorentzian lineshape raised to a power of the form of expression 2:

$$\Delta R/R(E) \sim A\ Re[e^{i\theta}E - E_g + i\Gamma]^{-m} \qquad 2$$

where:

A is an amplitude factor

θ is a lineshape phase factor $E_g$ is the transition energy

Γ is a broadening energy parameter m is a critical point transition dimensionality parameter, generally 2.5 or 3.0, but which is 2.0 in the case of an excitonic or other bound carrier transition.

Expressions describing the behaviour of the photoreflectance spectrum in cases where the semiconductor layer of interest has developed a sufficiently high in-built d.c. electric field to produce a measurable Franz-Keldysh oscillation effect, including those based on electro-optic functions derived from Airy functions and their derivatives, and simpler or related expressions approximating the asymptotic behaviour of the photoreflectance spectrum under similar electric field conditions.

Expressions (the so-called "linear analyzis" method) relating the spectral positions of successive Franz-Keldysh oscillation photoreflectance signal maxima and minima, and/or zero signal points, relative to the bandgap of a semiconductor, to the index of the said photoreflectance signal maxima and minima or zero, such that the slope of the graph of these two quantities yields and electro-optic energy.

Conversion expressions for the electro-optic energy determined by either of the foregoing methods, to the electric field in the semiconductor or near its interface or surface.

Expressions convolving the First Derivative Functional Form or other expressions the form of expression 2, with another expression representing Lorentzian lineshape representing the spectral variation of the reflectance or a mode of a reflecting cavity or etalon containing the semiconductor layer to be measured, as in the case of a vertical cavity surface emitting laser (VCSEL), for example. One example is the product of two expressions of form 2, one with exponent m=1 and the other with exponent m=2, which may be used to model the photoreflectance lineshape of the region of the cavity mode and quantum well energies in a VCSEL.

Similar expressions to the above which use a Gaussian lineshape rather than a Lorentzian lineshape as their basis.

These analyzes are preferably performed by a suitable algorithm preferably implemented using a computer program.

In some embodiments, the sample may be a semiconductor, semiconductor crystal structure, or a semiconductor wafer comprising one or more semiconductor devices and structures, and the pump beam is provided by a laser or other light source whose photon energy is at least greater than the fundamental bandgap energy of one of the semiconductors, and at least one photoreflectance lineshape is measured which corresponds to a direct interband transition also referred to as a direct bandgap or direct optical bandgap in the semiconductor layer which has generated it. This photoreflectance lineshape is analyzed to yield the energy of this direct interband transition. In some cases, the transition energies of direct intersubband transitions may also be determined. In some cases, the transition energies of quantum well or quantum dot transitions may also be determined. In some cases, the d.c. electric field within a semiconductor layer or portion thereof may also be determined from the analyzis of the photoreflectance spectrum or lineshape.

In another embodiment, at least two photoreflectance lineshapes are measured which correspond to at least two direct interband transitions also referred to as a direct bandgap or direct optical bandgap in either the same or different semiconductor layers which have generated them. These photoreflectance lineshapes are analyzed to yield the energy of these direct interband transitions. In some cases, the transition energies of direct intersubband transitions may also be determined. In some cases, the transition energies of quantum well or quantum dot transitions may also be determined. In some cases, the d.c. electric field within a semiconductor layer or portion thereof may also be determined from the analyzis of the photoreflectance spectrum or lineshape.

In one embodiment, the method includes the further steps of analyzing the energy of one or more of these direct interband transitions, measured by photoreflectance spectroscopy, to measure the strain in the semiconductor layer with which its origin is associated.

The method may include the further steps of analyzing the energy of one or more of these direct interband transitions, measured by photoreflectance spectroscopy, to measure the alloy mole fraction in the semiconductor layer to which it is associated.

The method may include the further steps of analyzing the energy of one or more of these direct interband transitions or quantum well or quantum dot transitions, measured by photoreflectance spectroscopy, to measure a spectral characteristic of the light emission from the semiconductor layer or structure to which it is associated.

The invention finds particular application to the measurement of strain in silicon, and especially anisotropic forms of strain including biaxial strain.

The invention is not limited to the embodiments described but may be varied in construction and detail. Certain embodiments of the invention may additionally comprise one or more of the following additional subsystems:

A modulation means in which the pump beam is spatially switched between a discrete path to coincidence with the probe beam on the sample and a discrete path which directs the beam to an area of incidence adjacent to the probe beam area of incidence, rather than turning off the pump beam, during the zero amplitude part of its cycle, to render any residual scattered light or luminescence from the sample as a d.c. signal which is not detected by lock-in amplification.

A probe beam normalisation detector subsystem, which may in some embodiments of the invention form part of the input probe beam subsystem, for detecting a portion of the light derived from the probe beam, together with coupling optics.

A microscopic optical means for reducing the diameter of the incidence spot of the light steered to the sample to the minimum size possible having regard to the limitations introduced by diffraction effects and the aberrations inherent in lens systems.

A polarising means for polarising the light steered to the sample, at different angles of polarisation relative to the plane of incidence of the light beam on the sample.

A probe beam optical intensity modulation means for modulating the intensity of the probe beam light, which would be used in conjunction with a more complex phase stepping algorithm in a double modulation system of the invention, which would have advantages in certain applications in which it is desired to recover the modulated reflectance signal from a larger modulated luminescence signal.

A variable angle of incidence mechanical means for mounting the input probe beam subsystem and output probe beam subsystem relative to a sample, which has a reflecting surface, such that the light beam from the input probe beam subsystem is reflected from the sample into the optical path of the output probe beam subsystem, and such that both said probe beam subsystems are mounted such that their optical axes make equal angles with a line normal to the surface of said reflecting sample, and such that said equal angles may be varied over a range from near normal incidence of the beam on the sample to a wide angle of incidence of the beam on the sample. The variable angle means may be used to exploit the dependence between the electro-optic function (i.e. the effective band mass and incidence angle) in order to obtain optimum measurement conditions to obtain the maximum signal from certain types of semiconductor sample, including cavity photonic structures and other multilayer structures.

A wafer manipulation subsystem for selecting a semiconductor wafer, which may have one of a range of diameters, from one or more cassettes or trays of such wafers, and placing said semiconductor wafer on said sample mounting subsystem such that a selected point on the wafer is at the point of incidence of the light beam from the input probe beam subsystem.

The electronics system in other embodiments may comprise multiple lock-in amplifiers, or a multi-channel lock-in amplifier having one channel per wavelength at which it is desired to measure the modulated reflectance signal.

A polariser in the path of the probe beam

A polariser in the path of the pump beam

Example

The following examples are not intended to limit the scope of the invention. In one specific example of the invention, a 300 W Oriel 6258 Ozone-Free Xenon arc lamp was used with reflecting and light collecting to produce a blue and near ultraviolet probe light beam, which was collimated and reflected from a silicon wafer and coupled to an Andor Shamrock SR303i Imaging Spectrograph, fitted with a grating with 600 lines per mm and blazed at 300 nm. To the exit port of the spectrograph was mounted a Hamamatsu S3921-512Q photodetector array. A Coherent 315M 150 mW diode-pumped solid state laser was amplitude modulated at a chopping frequency of 139 Hz using an Ametek optical chopper, and shone over the area of incidence of the probe light beam. A driver circuit designed for the S3921-512Q photodetector array was connected behind the array, and a special circuit designed to lengthen the output video-signal-type pulses from the array and driver circuit, was electrically connected to the output of the driver circuit. The output of the special circuit was connected to an analogue-to-digital converter card placed within a computer.

The spectrograph was set such that the wavelengths appearing on the 512 detector elements ranged from 459 nm to 326 nm, or in terms of photon energy, from 2.7 eV to 3.8 eV. The signal from the entire detector array of 512 pixels and its associated electronics was read, pixel-by-pixel, at a multiple of 7 times the chopping frequency of 139 Hz, repeatedly for a duration of 3.4 seconds. At photon energies near 3.39 eV, signals significantly in excess of a 3 ppm shot noise level were obtained, in a spectrum similar to that shown in the upper panel of FIG. 8. The spectrum thus obtained was fitted to equation 1 to yield a value of $E_g$=3.392 eV, corresponding to negligible strain of the silicon.

In another specific example of the invention, a 75 W Oriel 6247 Ozone-Free Xenon arc lamp was used with reflecting and light collecting optics to produce a blue and near ultraviolet probe light beam, which was collimated into a 400 micron core fused silica optical fibre, and the output beam from the optical fibre was collimated into a beam, which was reflected from a strained silicon on insulator wafer comprising a 200 Å thick strained silicon layer on a 1450 Å thick buried oxide layer on a bulk silicon substrate, and coupled to an Andor Shamrock SR303i Imaging Spectrograph, fitted with a grating having 600 lines per mm and blazed at 300 nm. To the exit port of the spectrograph was mounted a Hamamatsu S3901-512Q photodetector array. A Kimmon IK3802R-G HeCd 325 nm wavelength laser was amplitude modulated at a chopping frequency of 138.5 Hz using an Ametek optical chopper, and shone over the area of incidence of the probe light beam. A driver electronic circuit designed for the S3901-512Q photodetector array was electrically connected to the array, and a pulse generator circuit was electrically connected to the driver circuit. Electronic circuits comprising a special circuit designed to lengthen the output video-signal-type pulses from the detector array and driver circuit, an accumulator circuit, an analogue-to-digital converter circuit, and a programmable logic circuit comprising a programmable gate array, were electrically connected to the output of the driver circuit. These electronic circuits were connected to a computer using a universal serial bus (USB) cable and interface.

The spectrograph was set such that the wavelengths appearing on the 512 detector elements ranged from 459 nm to 326 nm, or in terms of photon energy, from 2.7 eV to 3.8 eV. The signal from the entire detector array of 512 pixels and its associated electronics was read, pixel-by-pixel, at a multiple of 7 times the chopping frequency of 138.5 Hz, repeatedly up to 4000 repeat acquisitions over a duration of 30 seconds. At photon energies near 3.3 and 3.4 eV, signals significantly in excess of a 5 ppm shot noise level were obtained, and a photoreflectance spectrum similar to that shown in the lower panel of FIG. 8 was obtained. The spectrum thus obtained was fitted to a summation of two lineshapes each described by the expression in equation 1 but having different parameters, to yield values of $E_g$=3.403 eV and $E_g$=3.302 eV, corresponding to a strain of 0.734% in the strained silicon layer.

Example Application

In one specific example of the invention, the photoreflectance spectrum of a strained silicon layer grown pseudomorphically on a silicon-germanium alloy of Ge alloy mole fraction 20.4%, is measured over the spectral range 2.8 eV to 3.6 eV at intervals of 0.002 eV. The spectrum is fitted to a summation of two low field photoreflectance lineshapes of the form of expression 1 above, and found to have an $E_1^+$ transition energy of 3.287 eV, shifted 105 meV from the $E_1$ transition energy of 3.392 eV of unstrained bulk silicon on the substrate of the same wafer. The shifts $\Delta E$ in each branch of the split $E_1$ transition energy and their relationship to the in-plane and out-of-plane strain tensor elements $\in_\perp$ and $\in_\parallel$ may be written in the form 3:

$$\Delta E = -3.267(\in_\perp + 2\in_\parallel) \pm 1.567(\in_\perp - \in_\parallel) \qquad 3$$

where the "±" sign is applied as "+" to obtain the shift in the $E_1^+$ branch and as "−" to obtain the shift in the $E_1^-$ branch, from the $E_1$ transition energy of unstrained silicon. Converted to in-plane strain using the expression 3, a value of 0.78% is determined for the in-plane strain of the top strained silicon layer.

The invention can also be used in a similar manner to determine the alloy mole fraction of silicon-germanium alloys. The known variance of the direct interband transition energies $E_1$ and $E_1 + \Delta_1$ in the region of 3.4 eV, valid for x<0.255, is given in 4 and 5

$$E_1(x) = 3.395 - 1.421x - 0.005x^2 \qquad 4$$

$$E_1 + \Delta_1(x) = 3.424 - 0.848x + 0.214x^2 \qquad 5$$

For the case of x=0, these relationships reduce to the direct interband transition energies of bulk silicon. These $E_1$ transitions appear as a single photoreflectance lineshape which gradually splits into a doublet lineshape both components of which are at lower transition energies with increasing germanium content in the silicon-germanium alloy.

Photoreflectance spectroscopy may be applied to measure and analyze the photoreflectance spectrum of a silicon-germanium alloy layer in a similar manner as described in the previous example, with the conversion of the $E_1$ transition energies to the Ge alloy mole fraction x using the relationships 4 and 5 above.

The foregoing examples illustrate how photoreflectance spectroscopy may be applied to measure strain and alloy mole fraction. Many other models of the behaviour of direct interband transition energies with parameters such as composition and strain of these and other semiconductors may be performed, and similar examples of the method of this invention carried out.

The invention provides an approach to making the photoreflectance spectrum measurement rapidly, by a simultaneous and/or multiplexed acquisition of the in-phase and quadrature photoreflectance signal and its phase at a multiplicity of wavelengths.

The invention overcomes a major difficulty with the prior art in the measurement of the photoreflectance spectrum in semiconductors, namely the slowness of the measurement because of the requirement for acquisition of the PR signal at each wavelength in sequence, in order to use lock-in amplification, and significantly advances the methods of modulation spectroscopy by disclosing a new method and apparatus for simultaneous, and/or multiplexed acquisition of in-phase and quadrature photoreflectance signal and its phase at all wavelengths of interest, using a phase stepping algorithm.

Another important advantage of this invention is that it is inherently fast. The measurement of the photoreflectance spectrum, typically composed of measurements at between 100 and 500 different wavelengths, can now be made in the time taken by prior art methods to measure at just one wavelength. A time saving, by this factor of 100 to 500 times faster results. Moreover, the speed of measurement makes practically feasible, the measurement of the photoreflectance spectrum at a multiplicity of locations on a semiconductor wafer, with a time duration which is considered reasonable in semiconductor production lines. The speed of measurement also allows a finer resolution to be achieved by reducing the wavelength interval of the spectral measurements, exploiting the advantages of an imaging spectrograph and high pixel density detector array. The additional advantage of the imaging spectrograph is to avoid the delay of moving parts in the system, particularly that of the scanning a monochromator grating as in a serial system.

The present invention therefore provides improved methods of photoreflectance spectroscopy.

Advantageous aspects which result from the improvements recited above are:

(a) Speed of measurement of a photoreflectance spectrum, improved by a factor of 100 to 500 typically compared to serial methods (b) Ability to make finer resolution measurements and wafer maps of photoreflectance spectra using the advantage of speed The photoreflectance spectrometer may comprise one of a number of means of modulating the reflectance and/or detecting the modulated reflectance signal.

The development of a method of parallel acquisition of the in-phase and quadrature photoreflectance signal and its phase, across a useful portion of the spectrum, which is simultaneous, and/or wavelength multiplexed, represents one of the most important improvements ever achieved in this field.

The invention finds general application in the following technical fields, among others:

Characterisation of semiconductor surfaces and interfaces

Characterisation of chemical, ion, electron, or plasma induced damage or modification effects in semiconductor layers and wafers or at their surfaces and interfaces Characterisation of semiconductor heterostructures and related devices.

Characterisation of strain effects in semiconductor layers and wafers

Measurement of surface and interfacial electric fields in semiconductor layers and wafers in certain types of semiconductor which exhibit Franz-Keldysh effects.

Measurement of the bandgap energy or interband transition energies of semiconductor layers Determination of strain from the bandgap energy or interband transition energies of semiconductor layers Measurement of the alloy mole fraction in compound semiconductor layers and wafers Measurement of the bandgap energy or interband transition energies of semiconductor layers composed of silicon, germanium, or alloys of silicon, germanium and carbon, and including insulating layers, and especially in ultrathin layer of silicon and silicon germanium-alloy where this invention enjoys special advantages over other methods of strain measurement.

Determination of strain and/or alloy mole fraction from the bandgap energy or interband transition energies of these semiconductor layers, and especially in ultrathin layer of silicon and silicon germanium-alloy where this invention enjoys special advantages over other methods of strain measurement.

Any of the measurements or characterisation applications listed above when performed as a function of the application of an external stress to the sample, such as a mechanical or thermal stress.

The sample may be a semiconductor, including one or more of the following semiconductor types, and may also have insulating or conducting regions or materials present thereon, such as silicon oxide or silicon nitride, or other dielectric layers, or may consist of an organic or inorganic material, which may include a polymeric material such as but not limited to:

Silicon
Germanium
Silicon-Germanium alloy
Silicon-Germanium-Carbon alloy
Silicon-Germanium alloy whether strained or not on Silicon
Silicon-Germanium-Carbon alloy whether strained or not on Silicon
Dielectric layer on Silicon
Dielectric layer on Germanium
Dielectric layer on Silicon-Germanium alloy
Dielectric layer on Silicon-Germanium-Carbon alloy
Silicon on insulating layer including silicon oxide layers on Silicon
Strained Silicon on Silicon-Germanium-Carbon alloy on Silicon
Strained Silicon on insulating layer including silicon oxide layers on Silicon
Strained Silicon on Silicon-Germanium alloy on insulating layer including silicon oxide layers on Silicon
Silicon-Germanium alloy whether strained or not on insulating layer including silicon oxide layers on Silicon
Germanium whether strained or not on Silicon-Germanium alloy
Germanium whether strained or not on Silicon
Silicon whether strained or not on Germanium whether strained or not
Gallium Arsenide
Aluminium Arsenide
Indium Phosphide
Aluminium Gallium Arsenide
Indium Gallium Arsenide
Aluminium Gallium Phosphide
Indium Gallium Phosphide
Aluminium Gallium Arsenide Phosphide
Indium Gallium Arsenide Phosphide
Indium Gallium Aluminium Phosphide
Gallium Nitride
Indium Nitride
Aluminium Nitride
Aluminium Gallium Nitride
Indium Gallium Aluminium Nitride
Cadmium Telluride
Cadmium Zinc Telluride
Zinc Oxide
Any combination of the above materials, whether strained or not, which may include a patterned wafer combination of the materials in an integrated circuit or a geometric test structure In most of the cases above the photoreflectance signal is obtained from the top semiconductor layer, but in some cases, a lower intensity signal may also be obtained from a lower semiconductor layer.

It will be appreciated that the invention discloses an improved method and apparatus for the measurement of many semiconductor properties by modulation spectroscopy. The method improves upon the prior art in providing a rapid acquisition method of photoreflectance spectroscopy by providing a method of acquiring the photoreflectance at all the wavelengths of interest, in a simultaneous, and/or multiplexed manner.

The invention claimed is:

1. An optical modulation spectroscopy system comprising:
a probe beam source;
a probe beam directed at a sample to give rise to a reflected probe beam;
a pump beam source;
a modulator for modulating a pump beam;
a modulated pump beam directed at a sample;
a dispersive system for dispersing the reflected probe beam into constituent wavelengths to provide dispersed beams; and
a detection system for detecting a plurality of the dispersed reflected probe beams, and for processing a signal corresponding to each, the detection system comprising:
an array of detectors and a circuit, with a detector for detecting each of at least some of said dispersed beams; and
wherein each detector produces as output an electrical signal which comprises both a DC signal, proportional to the reflectance of a dispersed beam and an AC modulated signal at the modulation frequency proportional to the modulation of the reflectance of a dispersed beam.

2. The system according to claim 1, wherein each detector is a photodetector pixel.

3. The system according to claim 1, wherein the DC signal is larger relative to the AC signal and the dynamic range of the detector is sufficient to detect both the DC signal and the AC signal.

4. The system according to claim 1, wherein the circuit provides clock and control pulses to the detectors and a synchronized reference waveform signal to the modulator.

5. The system according to claim 4, wherein the detection system measures each dispersed beam by multiplexed readout of signals from the detectors at a plurality of times at known phase steps during each period of the modulation, and the detection system calculates the photoreflectance signal using a phase stepping demodulation algorithm applied to the multiple measurements at the known phase steps during each period of the modulation, to give a photoreflectance spectrum.

6. The system according to claim 5, wherein the detection system determines components of the modulation frequency which are in-phase and quadrature relative to the phase of the reference signal, and determines the in-phase and quadrature photoreflectance signals ratio at a plurality of beam photon energies to give the photoreflectance spectrum.

7. The system according to claim 5, wherein the detection system adds an arbitrary phase angle to the phase step angle used in the phase stepping demodulation algorithm such that the entire modulated reflectance signal and the photoreflectance signal are adjusted such that they are in-phase with the reference signal.

8. The system according to claim 5, wherein the detection system performs a readout a plurality of times, each corresponding to a period of the modulation.

9. A modulation spectroscopy method carried out by a modulation spectroscopy system, the method comprising:
   directing a probe beam at a sample to give rise to a reflected probe beam;
   modulating a pump beam, and directing the modulated pump beam at the sample;
   dispersing the reflected probe beam with a dispersive system into constituent wavelengths to provide dispersed beams;
   detecting a plurality of the dispersed reflected probe beams with a detection system and processing a signal corresponding to each, with the detection system comprising:
      an array of detectors and a circuit, with a detector detecting each of at least one of said dispersed beams; and
      each detector produces as output an electrical signal which comprises both a DC signal, proportional to the reflectance of a dispersed beam and an AC modulated signal at the modulation frequency proportional to the modulation of the reflectance of a dispersed beam.

10. The method as claimed in claim 9, wherein the DC signal is larger relative to the AC signal and the dynamic range of the detector is sufficient to detect both the DC signal and the AC signal.

11. The method as claimed in claim 9, wherein the circuit provides clock and control pulses to the detectors and a synchronised reference waveform signal to the modulator.

12. The method as claimed in claim 11, wherein the detection system:
   measures simultaneously each dispersed beam by multiplexed readout of signals from the detectors at a plurality of times at known phase steps during each period of the modulation; and
   calculates the photoreflectance signal using a phase stepping demodulation algorithm applied to the multiple measurements at the known phase steps during each period of the modulation, to give a photoreflectance spectrum.

13. The method as claimed in claim 12, wherein the detection system:
   determines components of the modulated reflectance signal which are in-phase and quadrature relative to the phase of the reference signal; and
   determines the in-phase and quadrature photoreflectance signals ratio at a plurality of beam photon energies to give the photoreflectance spectrum.

14. The method as claimed in claim 12, wherein the detection system adds an arbitrary phase angle to the phase step angle used in the phase stepping demodulation algorithm such that the entire modulated reflectance signal and the photoreflectance signal are adjusted such that they are in-phase with the reference signal.

15. The method as claimed in claim 12, wherein the detection system performs a readout a plurality of times, each corresponding to a period of the modulation.

16. The method as claimed in claim 12, wherein a part of the photoreflectance spectrum varies in magnitude at different probe beam photon energies and comprises one or more photoreflectance lineshapes.

17. The method as claimed in claim 16, wherein the sample is a semiconductor,
   semiconductor crystal structure, or a semiconductor wafer comprising:
      at least one semiconductor device and structure; and
      the pump beam is provided by a light source whose photon energy is at least greater than the fundamental bandgap energy of one of the semiconductors; and
   at least one photoreflectance lineshape is measured which corresponds to a direct interband electronic transition in the semiconductor layer.

18. The method as claimed in claim 17, wherein the photoreflectance lineshape is analyzed to yield the energy of the direct interband electronic transition.

19. The method as claimed in claim 17, wherein the photoreflectance lineshape is analyzed to yield at least one of the energy, the broadening parameter, the amplitude and the phase of the direct interband electronic transition.

20. The method as claimed claim 16, wherein the photoreflectance lineshape is analyzed to yield a quantum well or quantum dot transition energy in part or all of the sample.

21. The method as claimed in claim 16, wherein the photoreflectance lineshape is analyzed to yield an intersubband transition energy in part or all of the sample.

22. The method as claimed in claim 16, wherein the photoreflectance lineshape is analyzed to yield an electric field strength in part or all of the sample.

23. The method as claimed in claim 16, wherein at least two photoreflectance lineshapes are measured which correspond to at least two direct interband electronic transitions in either the same or different semiconductor layers which have generated them, and the photoreflectance lineshapes are analyzed to yield at least one of the energy of these direct interband electronic transitions, an intersubband transition energy, a quantum well or quantum dot transition energy or the broadening parameter, the amplitude and the phase of these transitions, or an electric field strength in part of all of the sample.

24. The method as claimed in claim 16, further comprising analyzing the energy of at least one of the direct interband electronic transitions, measured by photoreflectance spectroscopy, to measure the strain in the semiconductor layer to which it is associated.

25. The method as claimed in any of claim 19, further comprising analyzing at least one of the energy, the broadening parameter, the amplitude and the phase, of at least one of the direct interband electronic transitions, measured by photoreflectance spectroscopy, to measure parameters relating to at least one of the crystallinity (damage/disorder) to the semiconductor or its surface.

26. The method as claimed in claim 16, further comprising analyzing the energy of one or more of the direct interband electronic transitions, measured by photoreflectance spectroscopy, to measure the alloy mole fraction in the semiconductor layer to which it is associated.

27. The method as claimed in claim 16, further comprising analyzing the energy of one or more of the direct interband or intersubband electronic transitions, measured by photoreflectance spectroscopy, to measure the sheet carrier concentration in the semiconductor layer to which it is associated.

28. The method as claimed in claim 16, further comprising:
performing the measurement at a multiplicity of angles of incidence; and
performing an analyzis of the photoreflectance spectra to determine the quantum well transition energy in a semiconductor structure which is constructed to have an optical cavity, such as a semiconductor structure used for making a laser diode, a light emitting diode, a vertical cavity surface emitting laser or a resonant cavity light emitting diode.

* * * * *